US010519071B2

(12) United States Patent
Efrati et al.

(10) Patent No.: US 10,519,071 B2
(45) Date of Patent: *Dec. 31, 2019

(54) LIGHTWEIGHT ASSEMBLABLE APPLIANCE WITH PLIANT EXOSKELETAL SUPPORT RESPECTIVE KIT-OF-PARTS AND METHOD FOR PRODUCTION OF BIOGAS AND LIQUID FERTILIZER

(71) Applicant: HOME BIOGAS LTD., Beit Yanai (IL)

(72) Inventors: Oshik Moshe Efrati, Beit Yanai (IL); Yair Teller, Clil (IL); Erez Lanzer, Cfar Chaim (IL); Shoham Zak, Givat Ela (IL)

(73) Assignee: HOME BIOGAS LTD, Beit Yanai (IL)

( * ) Notice: Subject to any disclaimer, the term of this patent is extended or adjusted under 35 U.S.C. 154(b) by 176 days.

This patent is subject to a terminal disclaimer.

(21) Appl. No.: 15/632,367

(22) Filed: Jun. 25, 2017

(65) Prior Publication Data
US 2017/0291858 A1   Oct. 12, 2017

Related U.S. Application Data

(63) Continuation-in-part of application No. 14/899,620, filed as application No. PCT/IB2013/061160 on Dec. 19, 2013, now Pat. No. 9,688,585.
(Continued)

(51) Int. Cl.
*C05F 17/02* (2006.01)
*C05G 3/00* (2006.01)
(Continued)

(52) U.S. Cl.
CPC .......... *C05F 17/0258* (2013.01); *C02F 3/28* (2013.01); *C02F 11/04* (2013.01); *C05F 9/02* (2013.01);
(Continued)

(58) Field of Classification Search
CPC ...... C12M 21/04; C12M 23/14; C12M 23/26; C12M 23/36; C12M 23/44; C12M 23/46; C12M 23/48; C12M 23/54
See application file for complete search history.

(56) References Cited

U.S. PATENT DOCUMENTS 5,651,890 A * 7/1997 Trost .................. C02F 3/28
                                                  210/603
7,186,339 B1 * 3/2007 Roos .................... A01C 3/023
                                                  210/603

(Continued)

FOREIGN PATENT DOCUMENTS

DE        8304514 U1 * 4/1986 ............ C12M 21/04

OTHER PUBLICATIONS

English language machine translation of DE 8304514U1 (Apr. 1986), pp. 1-13. Accessed Jun. 15, 2016. (Year: 2016).*

*Primary Examiner* — William H. Beisner
(74) *Attorney, Agent, or Firm* — Mark David Torche; Patwrite Law

(57) ABSTRACT

An assemblable appliance and method of recycling organic waste into biogas and liquid fertilizer, implementing essentially anaerobic digestion processes, is described. The assemblable appliance includes: a pliant structured exoskeletal envelope, pliable collapsible anaerobic digester and gas tank. A compact kit-of-parts for assembling the aforementioned appliance and respective method using the aforementioned appliance for recycling organic waste into biogas and liquid fertilizer are described.

20 Claims, 15 Drawing Sheets

Related U.S. Application Data

(60) Provisional application No. 61/916,246, filed on Dec. 15, 2013.

(51) Int. Cl.
*C05F 17/00* (2006.01)
*C05F 9/02* (2006.01)
*C12M 1/107* (2006.01)
*C12M 1/00* (2006.01)
*C12P 5/02* (2006.01)
*C02F 3/28* (2006.01)
*C02F 11/04* (2006.01)
*C02F 103/00* (2006.01)

(52) U.S. Cl.
CPC ...... *C05F 17/0018* (2013.01); *C05F 17/0205* (2013.01); *C05F 17/027* (2013.01); *C05F 17/0211* (2013.01); *C05F 17/0276* (2013.01); *C05G 3/0064* (2013.01); *C12M 21/04* (2013.01); *C12M 23/26* (2013.01); *C12M 23/36* (2013.01); *C12P 5/023* (2013.01); *C02F 2103/002* (2013.01)

(56) References Cited

U.S. PATENT DOCUMENTS

| | | | | |
|---|---|---|---|---|
| 7,669,727 | B2* | 3/2010 | Hubbard | B65D 61/00 206/522 |
| 9,688,585 | B2* | 6/2017 | Efrati | C05F 17/0027 |
| 2004/0045899 | A1* | 3/2004 | Humphrey | C02F 3/02 210/620 |

* cited by examiner

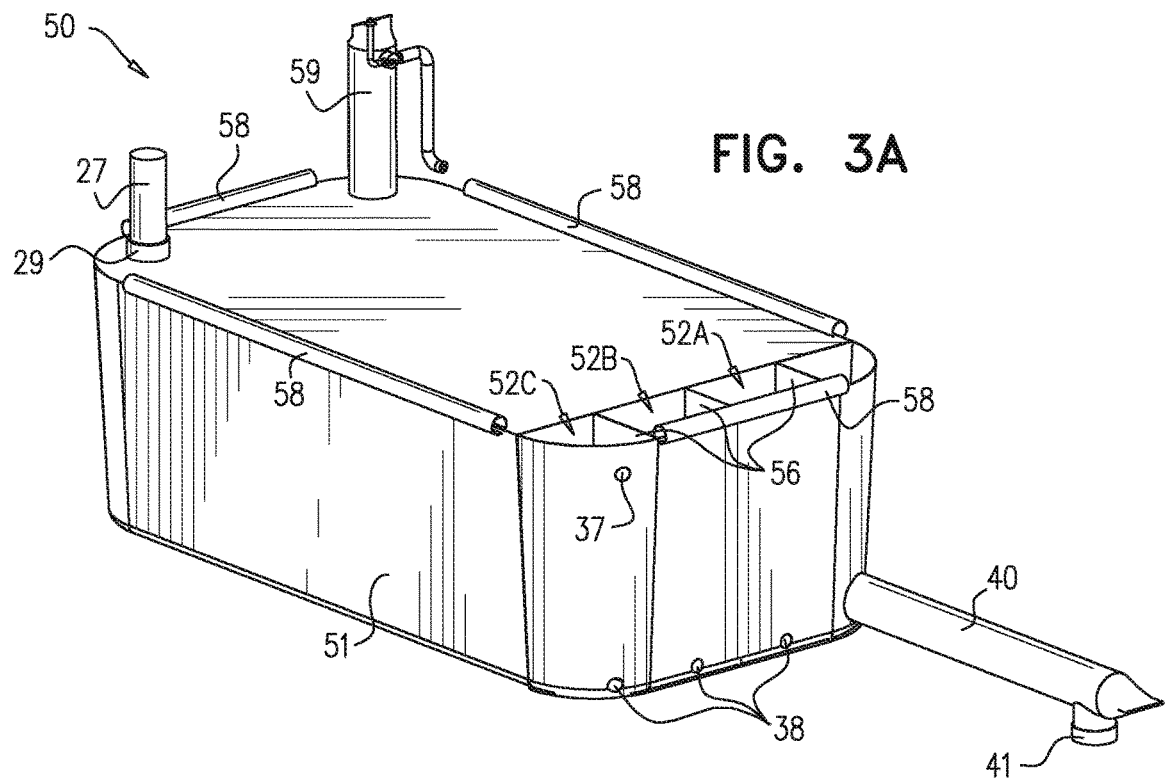
FIG. 3A
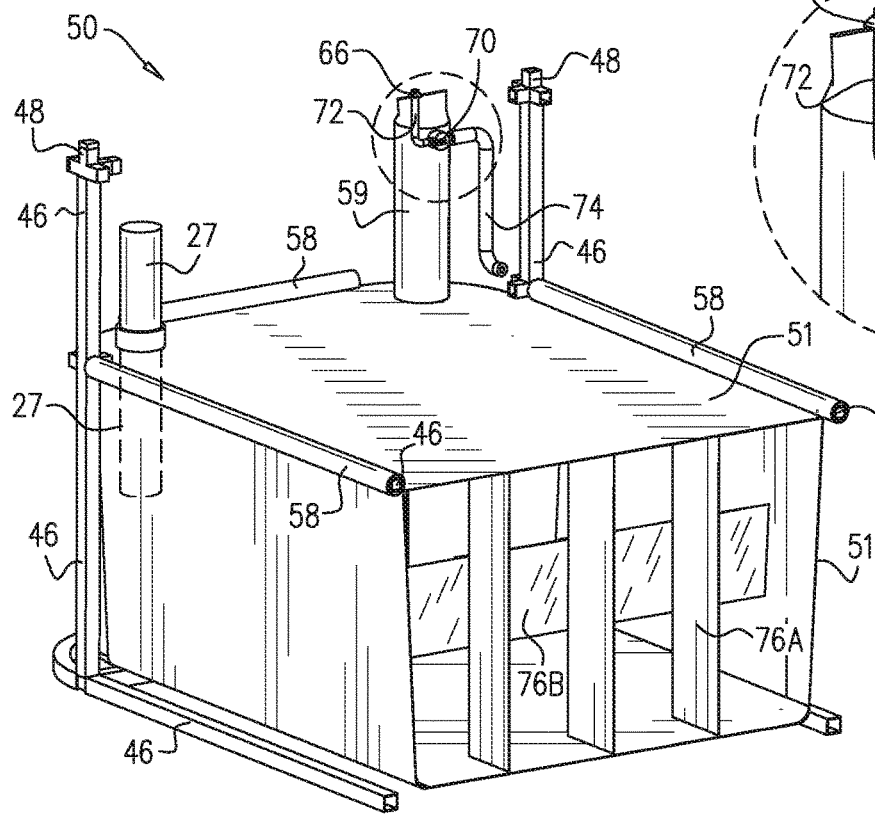
FIG. 3B
FIG. 3C

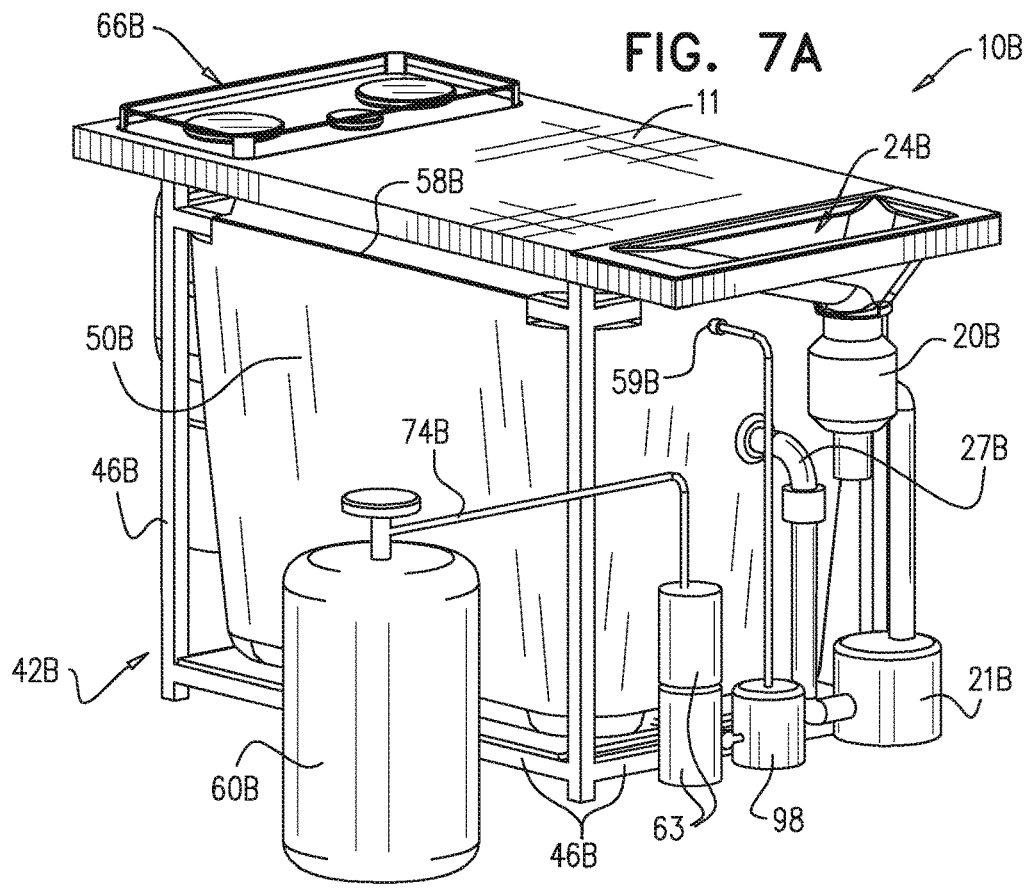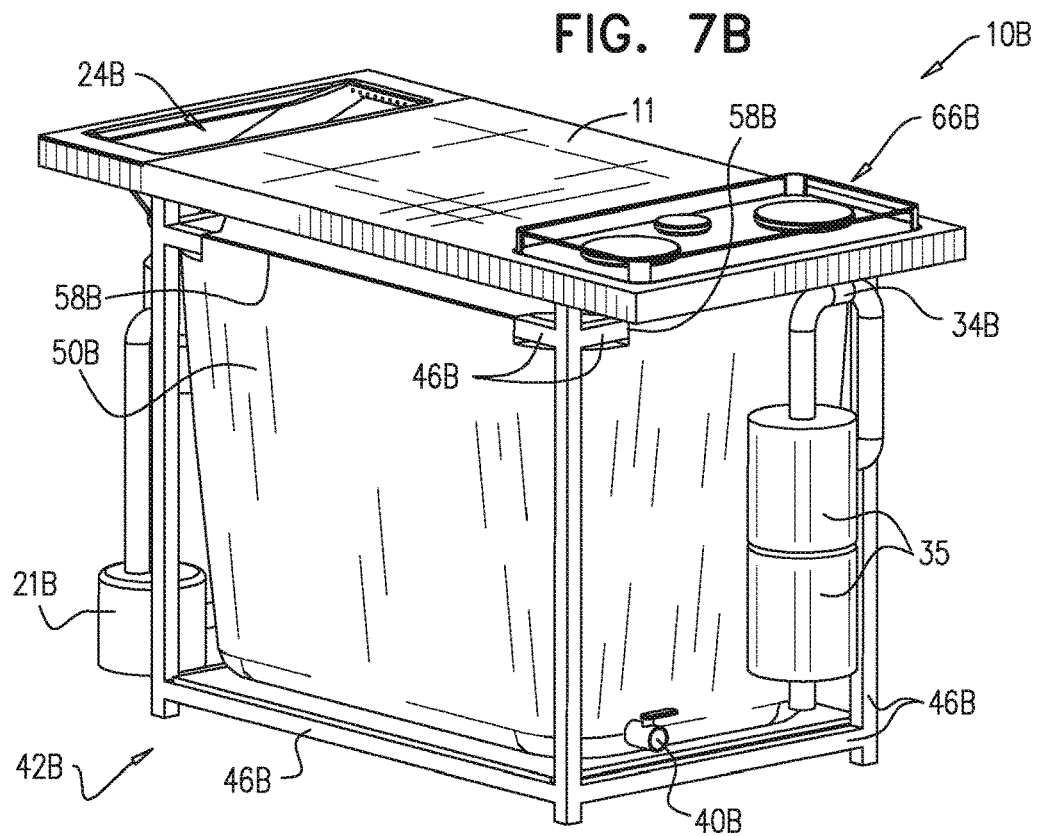

LIGHTWEIGHT ASSEMBLABLE APPLIANCE WITH PLIANT EXOSKELETAL SUPPORT RESPECTIVE KIT-OF-PARTS AND METHOD FOR PRODUCTION OF BIOGAS AND LIQUID FERTILIZER

CROSS REFERENCE TO RELATED APPLICATIONS

The present application is a continuation-in-part of Ser. No. 14/899,620 filed Dec. 18, 2015, which is a national phase of international PCT application IB2013/061160 filed Dec. 19, 2013, claiming the benefit of domestic priority from provisional application 61/916,246 filed Dec. 15, 2013 and Paris convention priority from international PCT application IB2013/001272 filed Jun. 18, 2013.

TECHNICAL FIELD

In general, the present invention pertains to systems and methods of recycling organic waste and utilizing the products thereof. In particular, the invention relates to a lightweight assemblable appliance, supported and shaped by a pliant structured exoskeletal envelope, implementable for recycling organic waste, implementing essentially anaerobic digestion processes.

BACKGROUND OF THE INVENTION

Household organic waste makes up a considerable percentage of total waste. This waste is typically thrown out with the rest of the garbage, requiring transport and space in dumps. Such waste is occasionally used for the purposes of producing compost, saving the transport and space requirements, as well as providing a source of rich soil. Hence improved system and methods for combined biogas and fertilizer production from such waste organic waste shall entail an environmental benefit.

Previous attempts include method and device, disclosed in international patent application PCT/ES2010/070120, publication number WO/2010/100309, used for the recycling and exploitation of biodegradable domestic waste produced in the dwellings of a community, by means of prefabricated biogas-production plants, in order to produce electricity and fertilizer and to heat water. The waste is ground in a grinder provided in the kitchen sinks and is conveyed, by means of a network separate from the sewage network, to a biogas-production plant formed by digesters, where biogas is produced by means of anaerobic digestion.

Yet previous attempts include method and device, disclosed in US2010/233778, for generating biogas from organic materials having a biogas reactor which has a charging chamber for being charged with the organic materials and a backflow channel for an at least partial discharge of the organic materials from the biogas reactor. According to US2010/233778 the biogas reactor in addition has at least one intermediate chamber, the charging chambers of which form at least one intermediate chamber and the backflow channel form in this sequence sections of a flow path through which flow can pass in only one direction for the organic materials, two sequentially following sections respectively forming a rising flow path in one case and a falling flow path in the other.

US2015/126349 which is believed to be the most pertinent prior art discloses a method for sealing and cutting of a flexible material for forming a flexible container comprising a product volume and at least one structural support volume can include feeding at least two flexible material into a sealing apparatus comprising a sealing surface and an opposed anvil surface; contacting a seam region of the at least two flexible material with the sealing surface to form a seal in the seam region and cut the seal to form a seam in a single unit operation. The seal in US2015/126349 defines one or both of at least a portion of a boundary of the product volume and at least a portion of a boundary of the at least one structural support volume.

It is further believed that the current state of the art is represented by U.S. Pat. Nos. 2,638,951, 5,429,437, 4,565,552, 5,924,461, 7,036,676 and 7,186,339; European patent EP0045114; Chinese patents and utility models CN201575295, CN201400673, CN201915092 and CN202576409, as well as by international patent applications having publication numbers WO2011133023 and WO2012153256.

SUMMARY OF THE INVENTION

In accordance with one aspect of invention there is provided a lightweight assemblable appliance, forming an autonomic standalone unit, for recycling organic waste into biogas and liquid fertilizer.

In accordance with another aspect of invention there is provided a method of producing biogas and liquid fertilizer by the means of lightweight assemblable appliance, implementing essentially anaerobic digestion processes.

In accordance with yet another aspect of invention there are provided systems and methods of sustaining fluent operation of the aforementioned lightweight assemblable appliance, as an autonomic standalone unit.

In accordance with still another aspect of invention there are provided systems and methods allowing convenient utilization of biogas and liquid fertilizer products resulting the digestion process.

In accordance with yet still another aspect of invention there is provided a lightweight appliance, for recycling organic waste into biogas and liquid fertilizer, assemblable from a compact kit-of-parts, convenient for shipment and deployment.

Definitions

The term assemblable, as referred to herein, is to be construed inter alia as capable of being assembled and deployed, rather readily and promptly, from a kit of respective parts.

The term assemblable, as referred to herein, is to be construed as including disassemblable or capable of being relatively easily dismantled or disassembled for relocation and/or redeployment.

The term assemblable, as referred to herein, is to be construed, inter alia, as providable or capable of being provided in a compact form as well as in dismantled or disassembled form.

Terms and expressions "in a compact form" or alike are to be construed as assuming a final construction size substantially larger than the size of aforesaid compact form.

The terms pliable or pliant, as referred to herein, are to be construed as having high tensile strength and capable of being efficiently flexed or bent but not being resilient and incapable of being efficiently stretched or expanded.

The terms elastic or resilient, as referred to herein, are to be construed as having tensile strength lower than aforesaid tensile strength of pliable or pliant material and optionally being capable of efficiently stretching or expanding.

The term exoskeletal, as referred to herein, is to be construed as being disposed exteriorly and providing structural support and/or firmness.

The term lightweight, as referred to herein, is to be construed as not exceeding 30 kilograms, whereas the term extremely lightweight is to be construed as preferably ranging between 15 and 25 kilograms.

The term compact size, as referred to herein, is to be construed as configured for shipment and transportation at the back seat of an economy car and/or by air cargo.

The terms sheet or fabric, as referred to herein, is to be construed inter alia any spun-melt or non-woven fabrics.

BRIEF DESCRIPTION OF THE DRAWINGS

The present invention will be understood and appreciated more comprehensively from the following detailed description taken in conjunction with the appended drawings in which:

FIG. 3A is an isometric view showing structural details of the anaerobic digester;

FIG. 3B is an isometric cross-sectional view of the anaerobic digester suspended from the structural scaffolding as well as of interior structural details of the former;

FIG. 3C is an enlarged isometric view of the gas supply assembly, shown in FIG. 3B;

FIG. 7A is a front perspective view of yet another embodiment of the lightweight assemblable appliance, configured for being built into a domestic kitchen;

FIG. 7B is a rear perspective view of the embodiment of the lightweight assemblable appliance, configured for being built into a domestic kitchen.

Figure 1A:
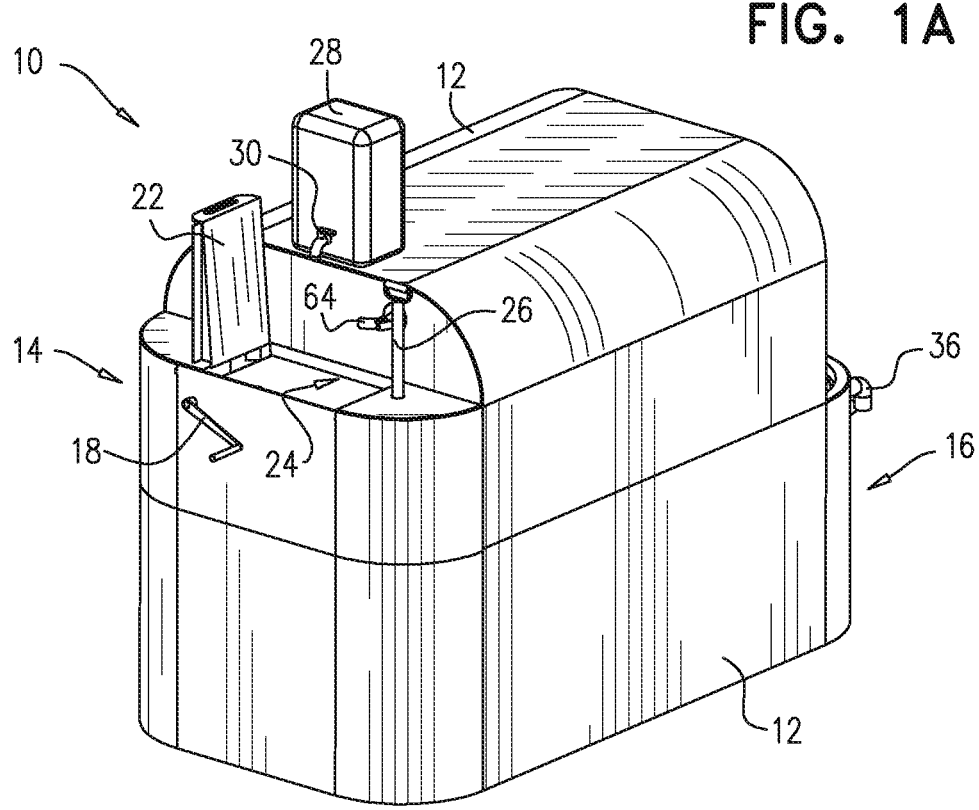
FIG. 1A is a front perspective view of an embodiment of a lightweight assemblable appliance for production of biogas and liquid fertilizer.

While the invention is susceptible to various modifications and alternative forms, specific embodiments thereof have been shown merely by way of example in the drawings. The drawings are not necessarily complete and components are not essentially to scale; emphasis instead being placed upon clearly illustrating the principles underlying the present invention.

DETAILED DESCRIPTION OF THE INVENTION

Illustrative embodiments of the invention are described below. In the interest of clarity, not all features of actual implementation are described in this specification. It will of course be appreciated that in the development of any such actual embodiment, numerous implementation-specific decisions must be made to achieve the developers' specific goals, such as compliance with technology- or business-related constraints, which may vary from one implementation to another. Moreover, it will be appreciated that the effort of such a development might be complex and time-consuming, but would nevertheless be a routine undertaking for those of ordinary skill in the art having the benefit of this disclosure.

In accordance with some embodiments of the present invention, reference is now made to FIG. 1A to 5, showing lightweight assemblable appliance 10, as well as structural details of the components thereof. Lightweight assemblable appliance 10 forms an autonomic standalone unit, utilized for recycling organic waste into biogas and liquid fertilizer. Preferably system 10 is assemblable with a minimal set of hand tools. System 10 is yet preferably assemblable by hand.

As shown particularly in FIGS. 1A-B and 2A-B, lightweight assemblable appliance 10 is covered by exterior enclosure 12. In an embodiment, exterior enclosure 12 is connected to and exterior to structural scaffolding 42. Exterior enclosure 12 typically comprises a transparent or translucent polymeric sheet, adapted to sustain a greenhouse effect, by capturing some of the solar energy. It is noted that lightweight assemblable appliance 10 employs essentially anaerobic and non-exothermic digestion processes. Therefore, an external source of heat is employed for sustaining an effective and fluent continuation of the anaerobic digestion processes, facilitated by the greenhouse effect of exterior enclosure 12. In some embodiments, exterior enclosure 12 comprising at least one detachable or partially detachable portion (not shown), configured to allow easy access to internal components of lightweight assemblable appliance 10, for maintenance and repair thereof. In some embodiments, an entirely or partially detachable portion of exterior enclosure 12 is fastened to the exterior enclosure 42 by a means of zip fastener, otherwise known as a clasp locker, hook and loop fastener, such as fastener commercialized under the trademark of VELCRO®, or similar means.

Figure 1B:
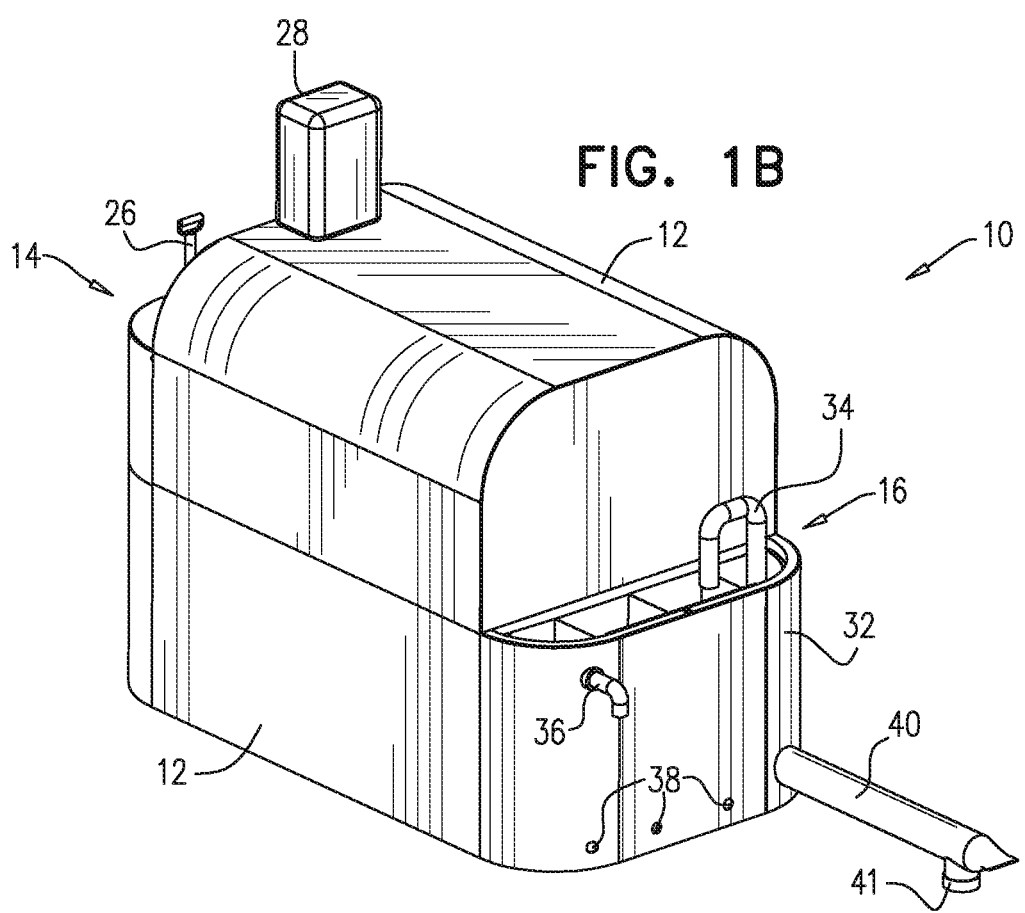
FIG. 1B is a rear perspective view of an embodiment of the lightweight assemblable appliance for production of biogas and liquid fertilizer.
Figure 1C:
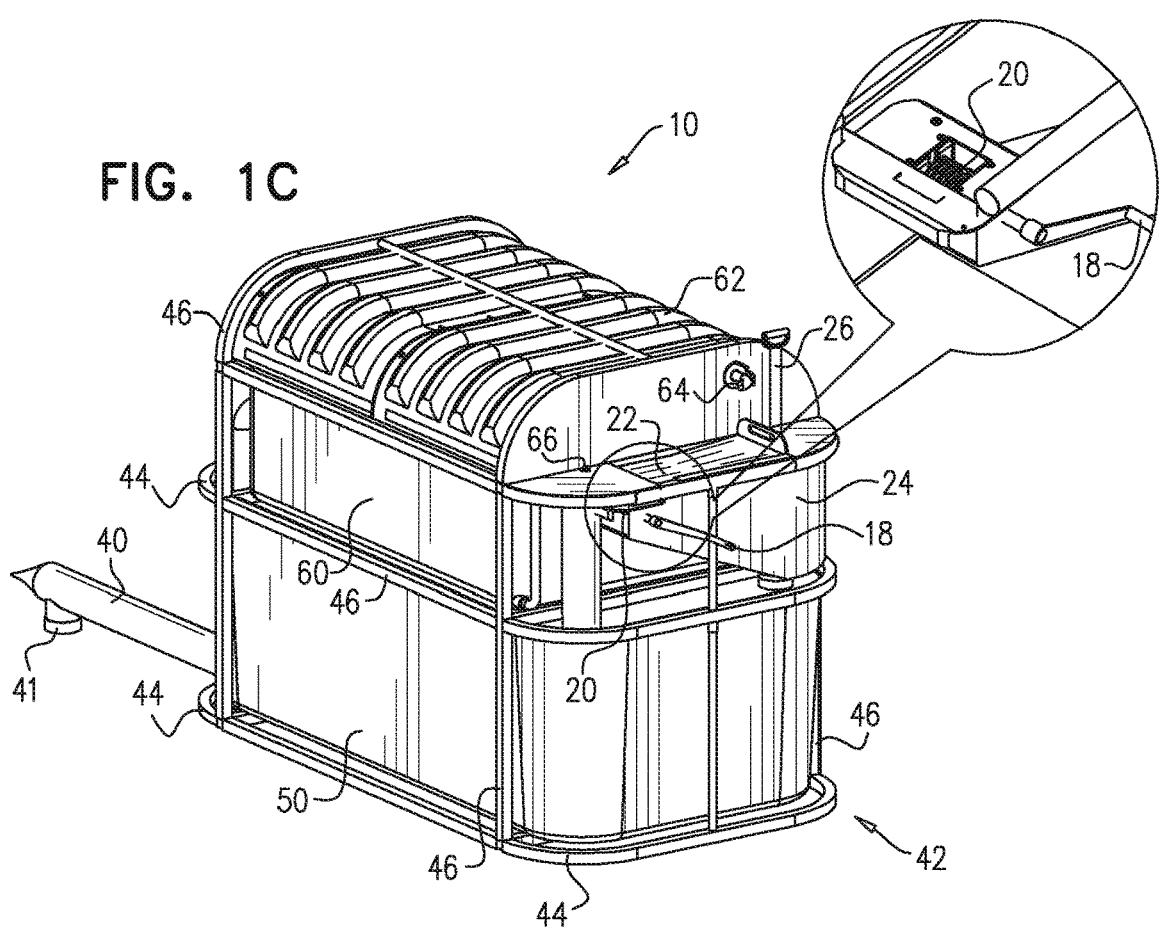
FIG. 1C is a front perspective view of an embodiment of the lightweight assemblable appliance, without the exterior enclosure, showing the interior components thereof.
Figure 1D:
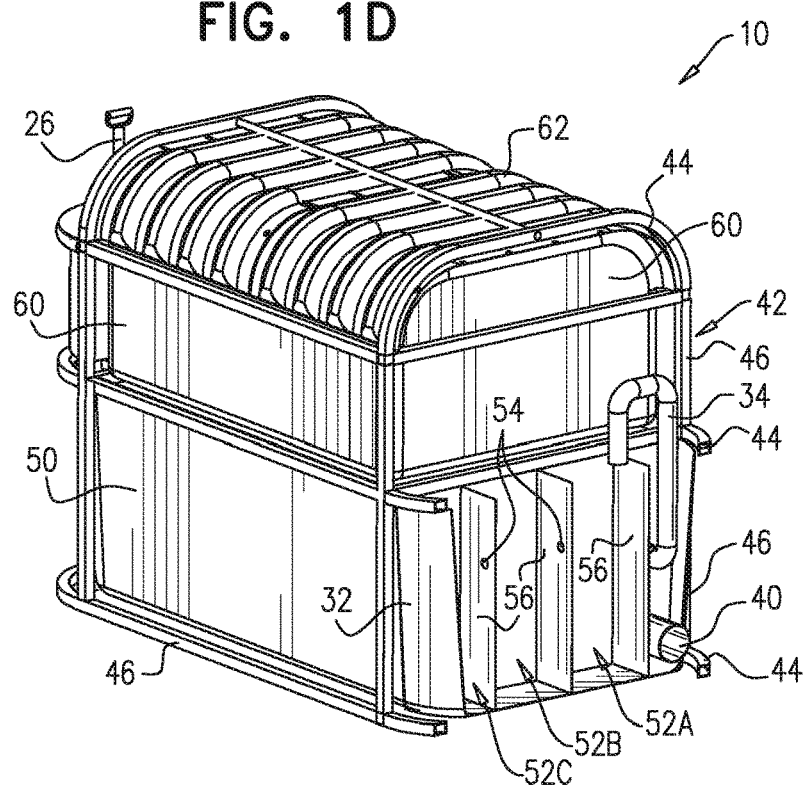
FIG. 1D is a perspective cross-sectional view of the back portion of an embodiment of the lightweight assemblable appliance, without the exterior enclosure.
Figure 2A:
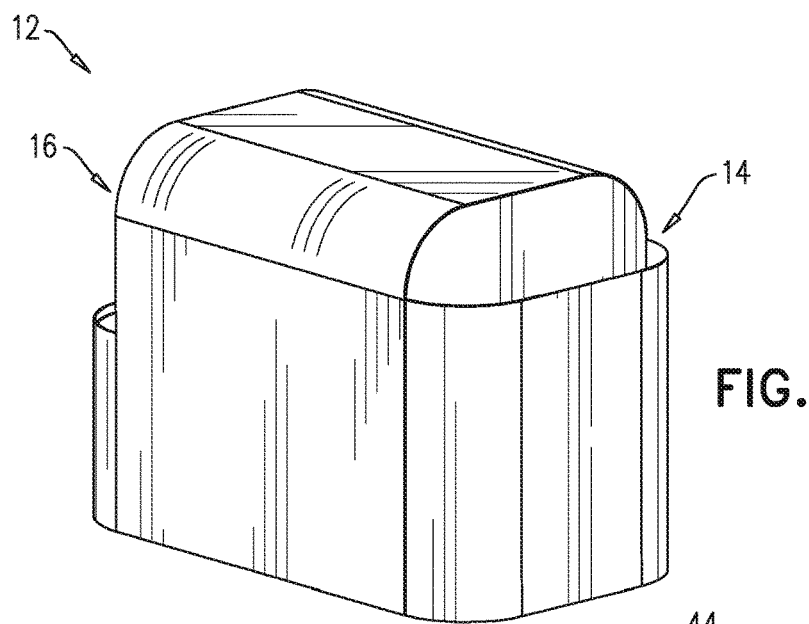
FIG. 2A is an isometric view of the exterior enclosure of an embodiment of the lightweight assemblable appliance.
Figure 2B:
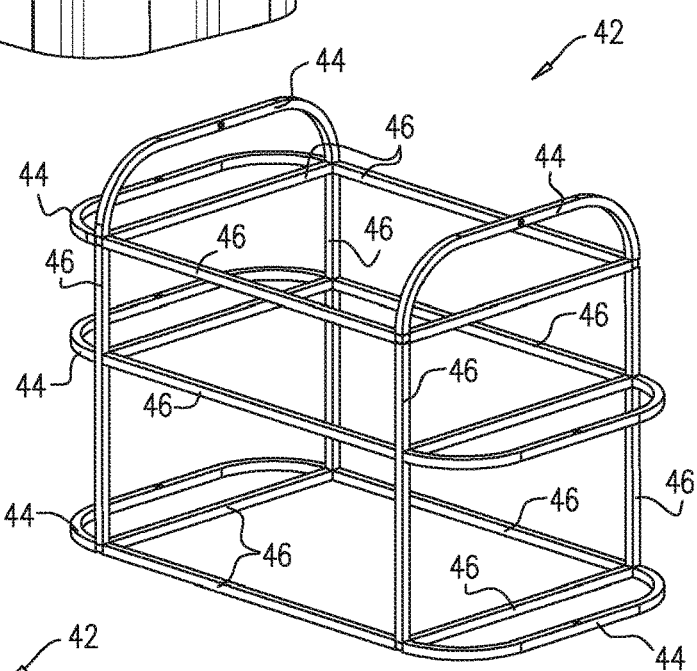
FIG. 2B is an isometric view of the structural scaffolding of an embodiment of the lightweight assemblable appliance, in an assembled conformation.
Figure 2C:
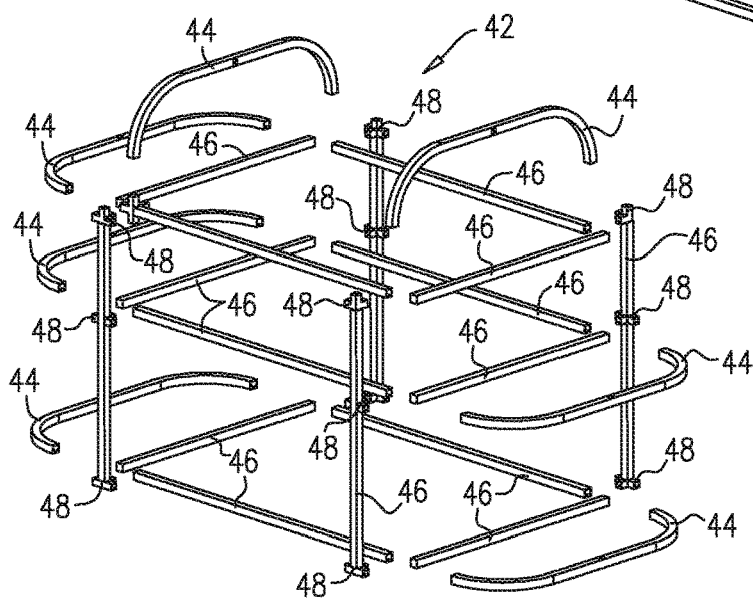
FIG. 2C is an isometric exploded view of the structural scaffolding, in a disassembled conformation.

Referring particularly to FIG. 1C-D, lightweight assemblable appliance 10 comprises anterior portion 14 and posterior portion 16. Anterior portion 14 and accommodates feeding sub-assembly comprising sink 24, grinder 20 and sink cover 22, as well as optionally fluid canister 28, or a fluid supply hose (not shown) disposed on top of sink 24, furnished with tap 30.

Grinder 20 shown in FIG. 1C is typically driven either manually, for instance by the means of handle 18, or by a motor (not shown) connected to a power source. Sink cover 22 comprises a sloped or slanted structure, adapted for conveniently feeding-in organic waste into grinder 20. In some embodiments sink cover 22 is pivotally attached to the edge of sink 24 adjacent to grinder 20, thereby allowing sink cover 24 to assume a horizontal and vertical conformations. In horizontal conformation, the sloped or slanted structure sink cover 22 facilitates convenient feeding-in of organic waste into grinder 20; whereas in vertical conformation sink cover 22 provides for access to the interior lumen of sink 24 allowing manually manipulating the contents of sink 24 towards the outlet thereof.

The aforementioned feeding sub-assembly is employed for processing an organic waste into a semiliquid mixture or slurry of ground organic matter and fluid, by grinding the organic waste (e.g. by grinder 20) and mixing the ground organic with fluid, controllably supplied via tap 30. The semiliquid mixture or slurry of ground organic matter and fluid is then fed into pliable collapsible anaerobic digester 50 through inlet pipe 27, which is connected to the outlet of sink 24. In one embodiment, anaerobic digester 50 is fed with fluids in a non-limiting manner including: water, grey water and slurry overflow fluid.

In some embodiments, alternative or additional sink (not shown), other than of sink 24, is used for animal droppings which are optionally utilized by lightweight assemblable appliance 10, typically without grinding. In such cases, there is a soaking treatment, in the alternative or additional sink or in a separate container.

Inlet pipe 27, shown in FIG. 3A-B, employed for feeding the semiliquid mixture or slurry of ground organic matter and fluid into anaerobic digester 50 is hermetically attached to anaerobic digester 50, so that the interior lumen of inlet pipe 27 forming a continuum with interior lumen of anaerobic digester 50. Inlet pipe 27 extends at least through a substantial portion of vertical dimension of anaerobic digester 50.

In an embodiment, multiple structural elements (not shown), such as flanges or pipe fittings, are attached to anaerobic digester 50 surfaces. In one embodiment, at least one inlet pipe 27 and or at least one slurry overflow outlet pipe 34 is/are connected to anaerobic digester 50 with such structural elements (not shown). In an embodiment, gas outlet pipe 59 is connected to anaerobic digester 50 with a structural member. In an embodiment, at least one sludge outlet pipe 40 is connected to anaerobic digester 50 with such a structural element.

It is noted that the anaerobic digestion processes occurring in pliable anaerobic digester 50 resulting a positive pressure therein, mainly of methane gas. Therefore a dedicated means is employed for feeding the aforementioned semiliquid mixture or slurry of ground organic matter and fluid into digester 50 under pressure. Various means are contemplated for accomplishing an effective feeding-in of the aforementioned semiliquid mixture or slurry of ground organic matter and fluid under pressure via inlet pipe 27, while preventing a backflow of gaseous or liquid contents out from anaerobic digester 50, in a non-limiting manner include: a screw pump, a piston manipulated by handle 26 or unidirectional valve disposed in inlet pipe 27.

In some embodiments, a piston manipulated by handle 26 includes a circumferential mitral skirt-like element, facilitating essentially unidirectional displacement of the aforementioned semiliquid mixture or slurry of ground organic matter and fluid relatively to the piston. In some embodiments, a handle 26 includes a floatation element (not shown) essentially lighter than the aforementioned semiliquid mixture or slurry of ground organic matter, thereby spontaneously driving handle 26 in an upward direction. In some embodiments a handle 26 further includes a plug (not shown), adapted for purposefully sealing the output of sink 24, while handle 26 is in a downward position; thereby providing for thwarting backflow leakage of the gas from anaerobic digester 50 as well as for controllably preventing advancement of the aforementioned semiliquid mixture or slurry of ground organic matter into inlet pipe 27 and allowing an aerobic pretreatment of aforementioned semiliquid mixture sink 24 for a predefined period of time.

In one embodiment, inlet pipe 27 is connected to a sidewall of anaerobic digester 50, such that the opening in the wall of anaerobic digester 50 is below the midline of the height of anaerobic digester 50.

As shown particularly in FIGS. 1B and 1D, system lightweight assemblable appliance 10 comprises posterior portion 16, which includes posterior compartment 32. Posterior compartment 32 forms an integral part of pliable collapsible anaerobic digester 50; however posterior compartment 32 optionally forms an individual part, attached to anaerobic digester 50. Posterior compartment 32 is optionally divided by partitions 56, into sub-compartments 52A, 52B and 52C. In one embodiment, apertures 54 in partitions 56 interconnect between sub-compartments 52A to 52C.

Sub-compartments 52A to 52C shown in 1B and 1D are adapted to encompass overflow of liquid fertilizer or slurry resulting the digestion processes in anaerobic digester 50. Liquid fertilizer or slurry is optionally spilled over, from slurry overflow outlet pipe 34, embodies a siphon configuration, extending from a sidewall of anaerobic digester 50 into sub-compartment 52A. Sub-compartments 52A to 52C, which are exposed to the ambient environment, are adapted to accommodate particular types of plants and microorganisms that function as a bio-filter. In one embodiment, the particular types of plants and microorganisms that are capable of reducing sulfur compounds in liquid fertilizer or slurry resulting the digestion processes in anaerobic digester 50; thereby preventing a notorious odor. Sub-compartment 52C optionally includes overflow outlet flange or pipe fitting 37, which is optionally further furnished with nozzle 36, adapted to controllably spill over any excessive liquid fertilizer or slurry resulting the digestion processes from sub-compartment 52C. Sub-compartments 52A to 52C are optionally furnished with sealable drainage apertures 38, adapted to allow conveniently emptying sub-compartments 52A to 52C upon opening of drainage apertures 38. In some embodiments, however there is at least one compartment such as 52A that functions as the bio-filter.

Posterior portion 16 further includes a sludge outlet draining pipe 40, shown in 1B and 1D, extending from a bottom portion of a sidewall of anaerobic digester 50, adapted for drainage of sludge and/or slurry resulting the digestion processes in anaerobic digester 50. Sludge outlet draining pipe 40 is preferably furnished with sealable cap or baffle 41, adapted for controllably opening/resealing sludge outlet draining pipe 40. Sludge outlet draining pipe 40 is pliable, allowing elevating the terminal portion thereof, thereby preventing the flow from anaerobic digester 50.

Lightweight assemblable appliance 10 comprises assemblable structural scaffolding 42 shown in 2B and 2C. Structural scaffolding 42 comprises a plurality of arcuate structural members 44 and a plurality of linear structural members 46, interconnected by connectors 48. Structural scaffolding 42 is assemblable from a compact kit-of-parts comprising arcuate structural members 44, linear structural members 46 and connectors 48. Structural scaffolding 42 is characterized by a relatively light weight and by compactness of the kit-of-parts used for assembling it; thereby rendering assemblable appliance 10 suitable for shipment and transportation in a rather compact disassembled form. Structural scaffolding 42 comprises at least one structural member adapted for suspending pliable collapsible anaerobic digester 50, as elaborated infra.

In one example, connectors 48 are embodied within terminal portions of structural members 44 and 46 and comprise an integral part of structural members 44 and 46. Structural members 44 and 46 thus interlock within each other, for instance by female and male endings of members 44 and 46; whereby multiple parts are connectable directly, without employing any individual connector 48 parts. In one embodiment, structural members 44 and 46 are profiles designed to provide increased bending strength. In one embodiment a couple of linear structural members 46 are provided as a singular L-shaped member. In another embodiment structural members form a closed shape such as a rectangle or ellipse.

Referring particularly to FIG. 3A-B, anaerobic digester 50 is preferably made of at least one sheet of pliable material 51, defining an essentially closed rectangular parallelepiped shaped structure; thereby rendering anaerobic digester 50 pliable and collapsible. It is emphasized that aforesaid essentially closed rectangular parallelepiped shaped structure is merely exemplary, whereas any pliable and collapsible closed geometrical shapes, in a non-limiting manner including: rectangular, cubical, cylindrical, discoid and globular or spherical closed structures, constitutes a legitimate variation of the pliable and collapsible anaerobic digester 50.

Anaerobic digester 50 shown in FIG. 3A-B is manufactured by welding of polymeric sheets. Therefore anaerobic digester 50 is capable of assuming a collapsed or folded conformation, suitable for shipment and transportation in a rather compact folded form. In other embodiments, however, anaerobic digester 50 is manufactured by welding and/or gluing segments polymeric sheets. In other embodiments, however, anaerobic digester 50 is manufactured by a means of molding, such as vacuum molding or blow molding.

Pliable collapsible anaerobic digester 50 shown in FIG. 3A-B comprises elongated suspension tabs 58 attached along edges of anaerobic digester 50. In one embodiment, elongated suspension tabs 58 are attached to the surfaces of anaerobic digester 50. In another embodiment, structural members 46 are threaded into elongated suspension tabs 58, thereby rendering anaerobic digester 50 suspendable from structural scaffolding 42. It is further noted that upon filling anaerobic digester 50 with the aforementioned semiliquid mixture or slurry of ground organic matter and fluid, while anaerobic digester 50 is suspended from structural scaffolding 42, stability is conferred to the structure of assemblable appliance 10 by the gravitational force exerted onto structural members 46 of scaffolding 42.

It is noted that the suspension tabs, such as tabs 58 shown in FIG. 3A-B, potentially embody a variety of shapes and/or structures as well as optionally include additional elements. The suspension tabs, such as tabs 58 optionally form an integral part of pliable collapsible anaerobic digester 50. Suspension tabs, as referred to herein, in a non-limiting manner include: a ring, an elongated sleeve, an abutment for attachment of another element, an element resembling a lifting ear.

In some embodiments, anaerobic digester 50 is suspended by straps and/or harness-like flexible structure (not shown), which are connected to structural scaffolding 42. In yet another embodiment, tab 58 comprises an extension of anaerobic digester 50 threaded into a slot in structural members 46.

Pliable collapsible anaerobic digester 50 shown in FIG. 3A-B further comprises gas outlet pipe 59, hermetically attached to an upper face of digester 50 and extending upwardly therefrom. Baffle 70 is connected to gas outlet pipe 59, for controlling distribution of gas (inter alia methane) accumulated under positive pressure in pliable anaerobic digester 50 as a result of anaerobic digestion processes occurring therein. Preferably the gas distribution system comprises safety valve 66, coupled to gas outlet pipe 59 and/or baffle 70 by conduit 72. Safety valve 66 is employed to release any excessive pressure of gas from anaerobic digester 50, upon exceeding a predetermined threshold. Gas distribution system further comprises conduit 74, coupling gas tank 60 to gas outlet pipe 59 and/or baffle 70.

In some embodiments, pliable collapsible anaerobic digester 50 comprises a plurality of tension struts, extending between surfaces of said essentially closed structure. In one embodiment, the tension struts are vertical and/or horizontal tension struts 76A and 76B, shown in FIG. 3A-B, extending in-between opposite walls or faces of anaerobic digester 50. Vertical and/or horizontal tension struts 76A and 76B are adapted to prevent excessive deformation or overstretching of anaerobic digester 50 upon buildup of gas pressure therein. In some embodiments, the struts are made from straps of pliable material.

In some embodiments, vertical and/or horizontal tension struts 76A and 76B as well as optionally the interior surface of the sidewalls of anaerobic digester 50 are furnished with a plurality of minute support structures, such as hair, fins or protrusions used to increase the interior surface area of anaerobic digester 50. The increase in surface area improves the distribution of bacteria throughout the fluid in digester 50. Bacteria have a tendency to sink, over time, to the lower fractions of the digester. The digester typically includes mechanisms used to stir the content fluid so that the bacteria rises and is more uniformly distributed throughout digester 50. The addition to the surface area on the vertical and/or horizontal tension struts 76A and 76B as well as optionally on internal walls of digester 50 postpones such sinking and thus renders the bacteria more productive.

Figure 5:
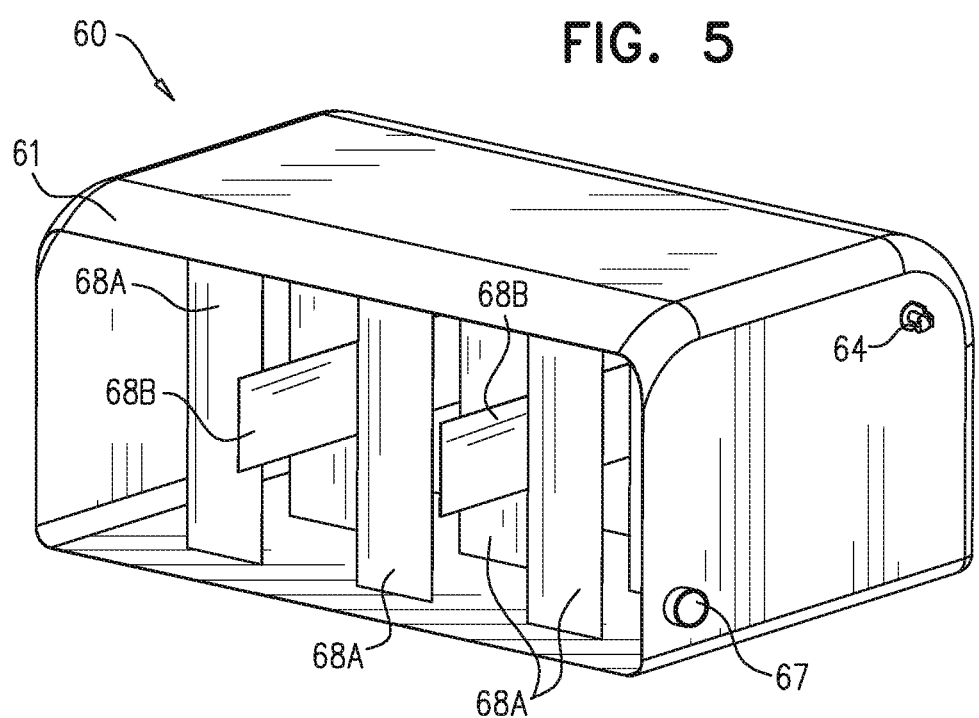
FIG. 5 is an isometric cross-sectional view showing structural details of the resilient gas tank.

Referring particularly to FIG. 5, lightweight assemblable appliance 10 comprises a resilient gas tank or bladder 60, employed to accumulate the gas produced by the anaerobic digestion processes tacking place in anaerobic digester 50 under positive pressure for subsequent use. Resilient gas tank 60 is typically disposed on top of anaerobic digester 50. In one embodiment, resilient gas tank 60 is detached from the structural scaffolding 42 while being connected to anaerobic digester 50 with a gas pipe 74. Resilient gas tank 60 is preferably made of at least one sheet of pliable and somewhat resilient material 61, defining an essentially closed structure; thereby rendering gas tank 60 collapsible as well as expandable or stretchable. Therefore resilient gas tank 60 capable of assuming a collapsed or depleted conformation, suitable for shipment and transportation in a rather compact folded form.

It is noted that resilient gas tank 60 shown in FIG. 5 can assume a variety of shapes, inter alia cylindrical, semi-cylindrical and a somewhat rectangular shape, optionally having at least a convex upper face. Resilient gas tank 60 comprises inlet 67 coupled by conduit 74 to the gas distribution system. Resilient gas tank 60 further optionally comprises gas outlet faucet 64, adapted to allow conveniently utilizing the gas. In one embodiment, there is at least one gas flange or gas pipe fitting structural element attached to resilient gas tank 60 surfaces. In some embodiments at least one inlet 67 and or at least one gas outlet valve 64 is connected to resilient gas tank 60 with a structural member.

In some embodiments, resilient gas tank 60 shown in FIG. 5 comprises a plurality of tension struts, extending between surfaces of said essentially closed structure. Wherein the tension struts are adapted to prevent excessive deformation or overstretching of pliable gas tank 60 upon buildup of gas pressure therein. In one embodiment, the tension struts are vertical and/or horizontal tension struts 68A and 68B, respectively, extending in-between opposite walls or faces of resilient gas tank 60. Vertical and/or horizontal tension struts 68A and 68B are adapted to prevent excessive deformation or overstretching of resilient gas tank 60 upon buildup of gas pressure therein.

Figure 4:
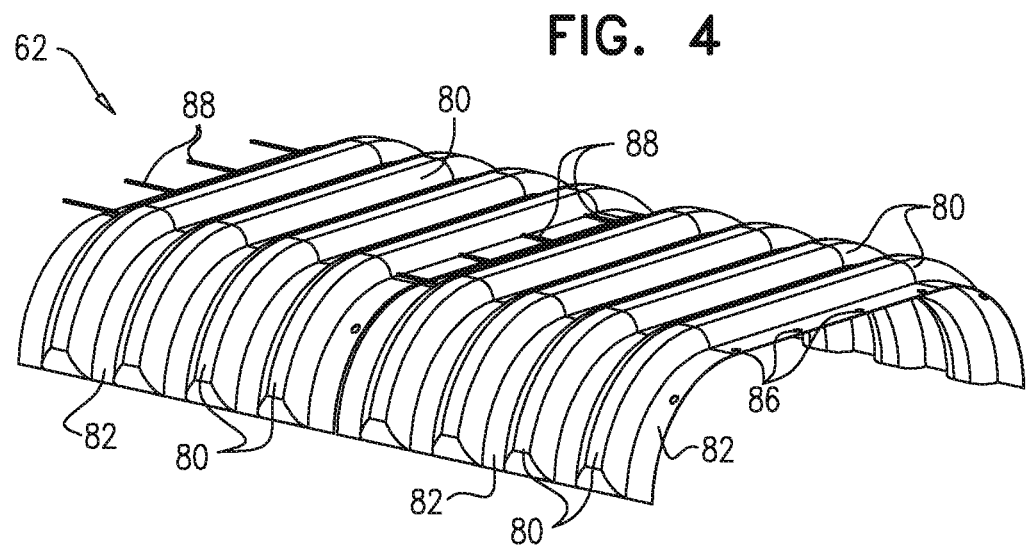
FIG. 4 is an isometric view of the ballast bags for a pliable gas tank.

Referring particularly to FIG. 4, lightweight assemblable appliance 10 comprises array 62 of elongated and foldable ballast bags 80. Array 62 of ballast bags 80 is employed to exert gravitational force onto convex upper face of resilient gas tank 60, thereby contributing to the positive pressure of the gas inside gas tank 60 and rendering the gas inside gas tank 60 readily available for utilization. Ballast bags 80 are fillable with ballast substance, typically having a relatively high density or weight to volume ratio, such as sand. In an embodiment, an array 62 of ballast bags 80 is capable of assuming an arcuate conformation, respectively conforming the surface of resilient gas tank 60. In one embodiment, array 62 of ballast bags 80 is capable of assuming a conformation, respectively conforming the shape of the top surface of pliable gas tank 60.

In one embodiment, ballast bags 80 shown in FIG. 5 are disposed on foldable bands 82, which are optionally include apertures 86 along the edges thereof. Interconnecting strips 88 are threaded into apertures 86 to adjoin a plurality of foldable bands 82 in tandem. Fillable ballast bags 80 of array 62 are capable of assuming a depleted conformation, suitable for shipment and transportation in a rather compact folded form. In some embodiment array 62 of ballast bags 80 is connected and/or forms an integral part of resilient gas tank 60.

Figure 6A:
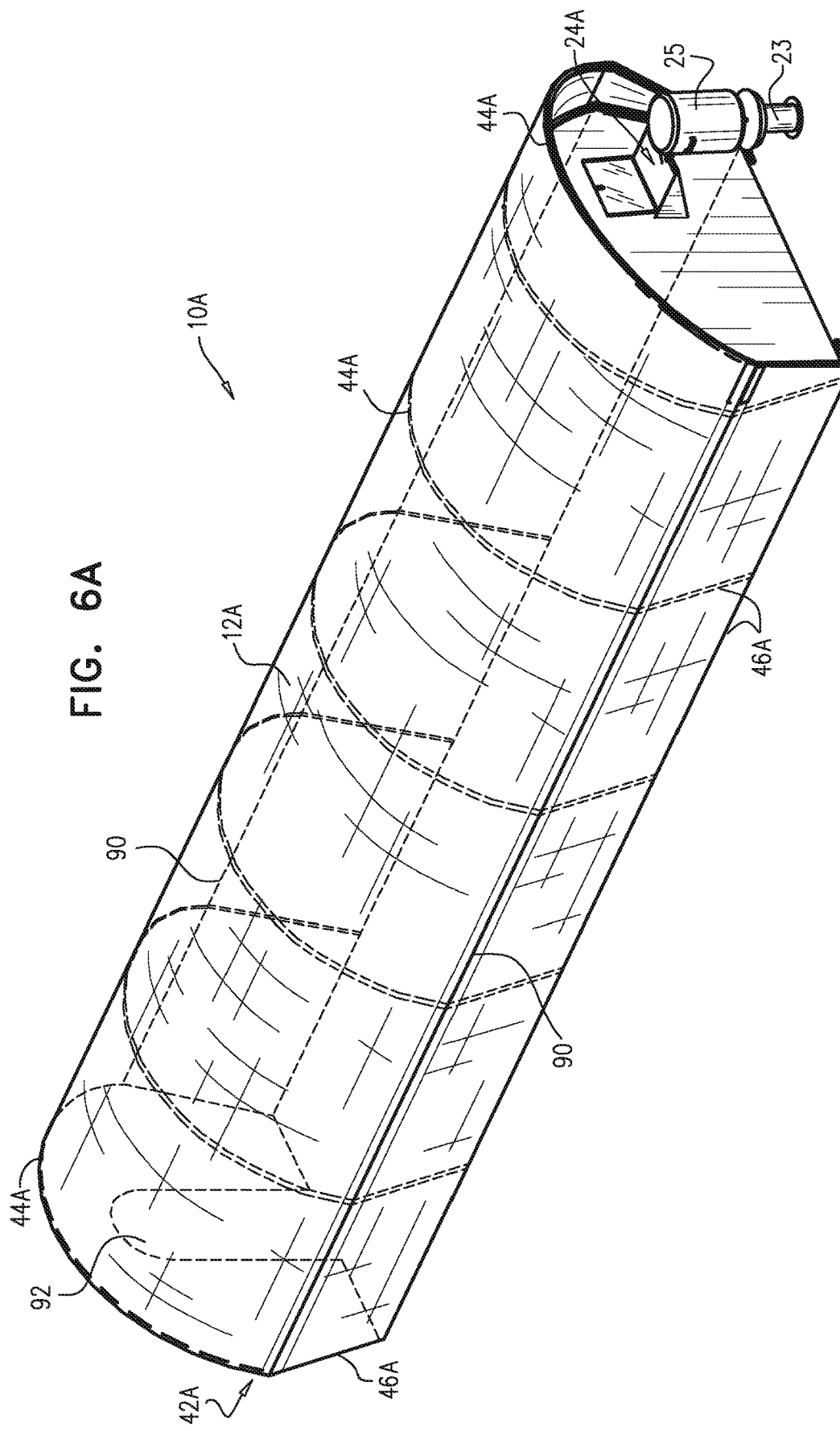
FIG. 6A is a front perspective view of another embodiment of the lightweight assemblable appliance, adapted for production of biogas and liquid fertilizer on institutional scale.
Figure 6B:
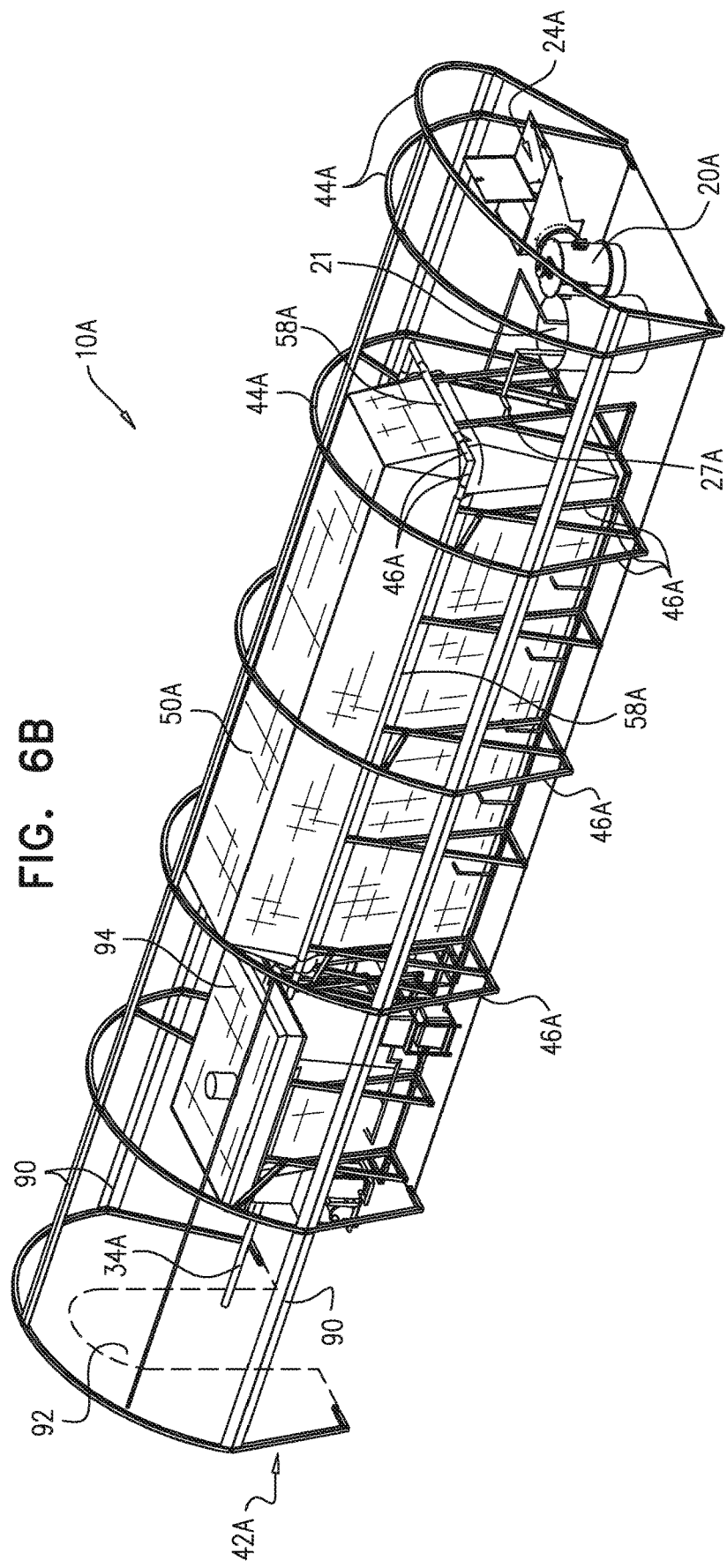
FIG. 6B is a front perspective view of another embodiment of the lightweight assemblable appliance of institutional scale, without the exterior enclosure, showing the interior components thereof.

In other embodiments assemblable appliance comprises appliance 10A, shown in FIGS. 6A and 6B, to which reference is now made, utilized for recycling organic waste into biogas and liquid fertilizer on a larger scale. Assemblable appliance 10A is utilized on an institutional or industrial scale. Recycling organic waste on an institutional or industrial scale entails the capacity of recycling up to hundreds of kilograms of organic waste per day. Assemblable appliance 10A, shown in FIGS. 6A and 6B, is typically connected to the institutional infrastructure, such as sewage, electricity as well as water and/or gas distribution pipe systems. In an embodiment system 10A is assemblable with a minimal set of hand tools. In yet another embodiment system 10A is assemblable by hand.

Lightweight assemblable appliance 10A, shown in FIGS. 6A and 6B, is adapted for recycling waste on institutional scale, is covered by exterior enclosure AJA. In an embodiment, exterior enclosure 12A typically comprises a transparent or translucent polymeric sheet, adapted to sustain a greenhouse effect, by capturing some of the solar energy. In an embodiment, exterior enclosure 12A comprises a thermal insulting material. Since lightweight assemblable appliance 10A employs essentially anaerobic and non-exothermic digestion processes, an external source of heat is employed for sustaining an effective and fluent continuation of the anaerobic digestion processes, facilitated inter alia by the greenhouse effect of exterior enclosure 12A. In some embodiments, exterior enclosure 12A comprising at least one detachable portion (not shown), allowing easy repair or replacement of an individual portion or segment of enclosure 12A.

Lightweight assemblable appliance 10A shown in FIGS. 6A and 6B includes an anterior portion, accommodating a feeding sub-assembly comprising sink 24A, grinder 20A and aerobic pre-treatment tank 21, as well as a water supply (not shown). Feeding sub-assembly optionally further comprises an organic waste dumper container 25, used to accumulate the organic waste throughout the day and scale weight 23, employed to evaluate the weight of organic waste in dumper container 25. Grinder 20A is typically driven by a motor (not shown) connected to a power source and optionally includes a screw pump for conveying the organic waste from sink 24A, into grinder 20A.

The aforementioned feeding sub-assembly is employed for processing an organic waste into a semiliquid mixture or slurry of ground organic matter and water, by grinding the organic waste (e.g. by grinder 20A) and mixing the ground organic matter with water. The semiliquid mixture or slurry of ground organic matter and water is then subjected to an aerobic pretreatment, for about 24 hours, prior to been fed into pliable collapsible anaerobic digester 50A through inlet pipe 27A, which is connected to the outlet of aerobic pre-treatment tank 21.

Lightweight assemblable appliance 10A shown in FIGS. 6A and 6B comprises assemblable structural scaffolding 42A. Structural scaffolding 42A comprises a plurality of arcuate structural members 44A and a plurality of linear structural members 46A, interconnected by connectors (not shown). Structural scaffolding 42A is assembled by affixing a plurality of arco-linear frames, typically comprising at least one arcuate structural member 44A and several linear structural members 46A of different lengths, in tandem along longitudinal beams 90. Longitudinal beams 90 are optionally modular or assemblable from segments.

Structural scaffolding 42A is assemblable from a compact kit-of-parts comprising arcuate structural members 44A, linear structural members 46A as well as optionally connectors (not shown) and/or longitudinal beams 90. Structural scaffolding 42 is characterized by a relatively light weight and by compactness of the kit-of-parts used for assembling the same; thereby rendering assemblable appliance 10A suitable for shipment and transportation in a rather compact disassembled form, frequently requiring less than a single marine shipment payload container.

Structural scaffolding 42A shown in FIGS. 6A and 6B comprises at least one structural member adapted for suspending pliable collapsible anaerobic digester 50A, as elaborated infra. Structural scaffolding 42A of assemblable appliance 10A preferably comprises the components for constructing a terminal arco-linear frame, embodying the shape of doorjamb 92. Doorjamb 92 disposed in terminal posterior arco-linear frame structural scaffolding 42A is used for mounting a door (not shown) allowing a controllably closable walking-through access into the posterior portion of assemblable appliance 10A.

Assemblable appliance 10A shown in FIGS. 6A and 6B comprises anaerobic digester 50A which is preferably made of a sheet of pliable material, defining an essentially closed rectangular parallelepiped shaped structure; thereby rendering anaerobic digester 50A pliable and collapsible. Anaerobic digester 50A is preferably manufactured by welding of polymeric sheets, however, in some instances anaerobic digester 50A is manufactured by welding and/or gluing segments polymeric sheets or by a means of molding, such as vacuum molding or blow molding. Anaerobic digester 50A is capable of assuming a collapsed or folded conformation, suitable for shipment and transportation in a rather compact folded form. It is once again emphasized that aforesaid essentially rectangular parallelepiped shaped structure is merely exemplary, whereas any pliable and collapsible closed geometrical shapes, in a non-limiting manner including cylindrical, discoid and globular or spherical closed structures, constitutes a legitimate variation of the pliable and collapsible anaerobic digester 50.

Pliable collapsible anaerobic digester 50A shown in FIGS. 6A and 6B comprises elongated suspension tabs 58A attached along edges of anaerobic digester 50A. Structural members 46A are threaded into elongated suspension tabs 58A, thereby rendering anaerobic digester 50A suspendable from structural scaffolding 42A. It is further noted that upon filling anaerobic digester 50A with the aforementioned semi-liquid mixture or slurry of ground organic matter and water, while anaerobic digester 50A is suspended from structural scaffolding 42A, stability is conferred to the structure of assemblable appliance 10A by the gravitational force exerted onto structural members 46A of scaffolding 42A.

It is noted that the suspension tabs, such as tabs 58A shown in FIG. 6B, potentially embody a variety of shapes and/or structures as well as optionally include additional elements. The suspension tabs, such as tabs 58A optionally form an integral part of pliable collapsible anaerobic digester 50A. Suspension tabs, as referred to herein, in a non-limiting manner include: a ring, an elongated sleeve, an abutment for attachment of another element, an element resembling a lifting ear. In some embodiments, anaerobic digester 50 is suspended by straps and/or harness-like flexible structure, which are connected to structural of scaffolding 42. In yet another embodiment, tab 58 comprises an extension of anaerobic digester 50 threaded into a slot in structural members 46.

Posterior portion of assemblable appliance 10A, at the rear of anaerobic digester 50A, comprises aerobic bio-filter 94 shown in FIG. 6B. Bio-filter 94 is a scaled-up embodiment of posterior compartment 32 of lightweight assemblable appliance 10 shown in FIG. 1 A-D, adapted to encompass overflow of liquid fertilizer or slurry resulting the digestion processes in anaerobic digester 50A. Liquid fertilizer or slurry is optionally supplied into bio-filter 94, by a slurry overflow outlet pipe, extending from a sidewall of anaerobic digester 50A. Bio-filter 94 is typically supplied with air for the ambient environment and adapted to accommodate particular types of microorganisms and or plants. In one embodiment, the microorganisms and or plants that are capable of reducing sulfur compounds in liquid fertilizer or slurry resulting the digestion processes in anaerobic digester 50A; thereby preventing a notorious odor. The liquid fertilizer or slurry is output from bio-filter 94 via slurry outlet pipe 34A.

Assemblable appliance 10A shown in FIG. 6B further comprises a gas outlet pipe, hermetically attached to an upper portion of anaerobic digester 50A and a sludge outlet draining pipe, extending from a bottom portion thereof. The gas outlet pipe is typically connected to a compressor, supplying compressed biogas into the institutional distribution system; whereas the sludge outlet draining pipe is typically connected to the institutional sewage. Assemblable appliance 10A optionally includes a pipe system and/or manifold, disposed at the bottom portion of digester 50A, used to recirculate a portion of the biogas throughout anaerobic digester 50A thereby stirring up the contents thereof.

In other embodiments, lightweight assemblable appliance 10B, shown in FIGS. 7A and 7B, to which reference is now made, is adapted for been built into standard domestic kitchen. Assemblable appliance 10B, shown in FIGS. 7A and 7B, adapted for been built into or form a part of a standard domestic kitchen, is typically connected to the domestic infrastructure, such as sewage, electricity as well as water and/or gas distribution pipe systems.

Lightweight assemblable appliance 10B, shown in FIGS. 7A and 7B adapted for been built into a standard domestic kitchen, is typically covered by exterior panels (not shown) which are optimally supplied by the user, so as to fit or form a consistent interior design of the kitchen. Since lightweight assemblable appliance 10B employs essentially anaerobic and non-exothermic digestion processes, an external source of heat is preferably employed for sustaining an effective and fluent continuation of the anaerobic digestion processes, facilitated for instance by a controlled electric heater (not shown).

Lightweight assemblable appliance 10B includes working surface 11 shown in FIGS. 7A and 7B, from which organic waste is directly put into the feeding sub-assembly at the anterior portion assemblable appliance 10B, comprising dedicated sink 24B, grinder 20B and sludge pump 21B, as well as a water supply (not shown). Grinder 20B is typically a standard domestic garbage disposer driven by an electric motor (not shown) connected to sink 24B. The aforementioned feeding sub-assembly is employed for processing organic waste into a semiliquid mixture or slurry of ground organic matter and water, by grinding the organic waste (e.g. by garbage disposer 20B), mixing the ground organic matter with water and further feeding the resultant semiliquid mixture or slurry, for instance by sludge pump 21B, via inlet pipe 27B, into anaerobic digester 50B.

Lightweight assemblable appliance 10B comprises structural scaffolding 42B shown in FIGS. 7A and 7B which is typically assemblable from a compact kit-of-parts. Structural scaffolding 42B is characterized by a relatively simple construction and hence in some embodiments, structural scaffolding 42B is not assemblable, as referred to herein, but rater built by the installers while constructing the kitchen. Structural scaffolding 42B comprises a plurality of linear structural members 46B, optionally interconnected by connectors (not shown). Structural scaffolding 42B comprises at least one structural member adapted for suspending pliable collapsible anaerobic digester 50B.

Assemblable appliance 10B comprises anaerobic digester 50B shown in FIGS. 7A and 7B which is preferably made of at least one sheet of pliable material, defining an essentially closed rectangular parallelepiped shaped structure; thereby rendering anaerobic digester 50A pliable and collapsible. Anaerobic digester 50B is manufactured as set forth hereinabove.

In an embodiment pliable collapsible anaerobic digester 50B comprises elongated suspension tabs 58A attached along edges of anaerobic digester 50B. In an embodiment, elongated suspension tabs 58A are attached on surfaces of anaerobic digester 50B. Structural members 46B are threaded into elongated suspension tabs 58B, thereby rendering anaerobic digester 50B suspendable from structural scaffolding 42B.

It is noted that the suspension tabs, such as tabs 58B shown in FIGS. 7A and 7B, potentially embody a variety of shapes and/or structures as well as optionally include additional elements. The suspension tabs, such as tabs 58B optionally form an integral part of pliable collapsible anaerobic digester 50B. Suspension tabs, as referred to herein, in a non-limiting manner include: a ring, an elongated sleeve, an abutment for attachment of another element, an element resembling a lifting ear.

Posterior portion of assemblable appliance 10B, at the rear of anaerobic digester 50B, comprises filter 35 shown in FIGS. 7A and 7B. Filter 35 is adapted to drain overflow of liquid fertilizer or slurry resulting the digestion processes in anaerobic digester 50B. Liquid fertilizer or slurry is supplied into filter 35, by a slurry overflow outlet pipe 34B, preferably embodying a siphon configuration, extending from a sidewall of anaerobic digester 50B. Filter 35 is typically capable of reducing and/or removing sulfur compounds in liquid fertilizer or slurry resulting the digestion processes in anaerobic digester 50B; thereby preventing a notorious odor. The liquid fertilizer or slurry is output from filter 35 via slurry outlet pipe 34B which is optionally connected or connectable to the domestic sewage system.

Assemblable appliance 10B shown in FIGS. 7A and 7B further comprises a gas outlet pipe 59B, hermetically attached to an upper portion of anaerobic digester 50B and a sludge outlet draining pipe 40B, extending from a bottom portion thereof. Gas outlet pipe 59B is typically connected to a compressor 98. Compressor 98, which is typically actuated by a pressure sensor, upon attaining a predetermined level, compresses biogas, pushes compressed biogas through filters and/or dehydrators 63. Thereafter compressed filtered and/or dehydrated biogas is supplied via conduit 74B into gas into domestic gas tank 60B, from which is optionally supplied to burner unit 66B. Sludge outlet draining pipe 40B is typically connected to the domestic sewage system. Assemblable appliance 10B optionally includes a pipe system and/or manifold, disposed at the bottom portion of digester 50A, used to recirculate a portion of the biogas throughout anaerobic digester 50A thereby stirring up the contents thereof.

Figure 8A:
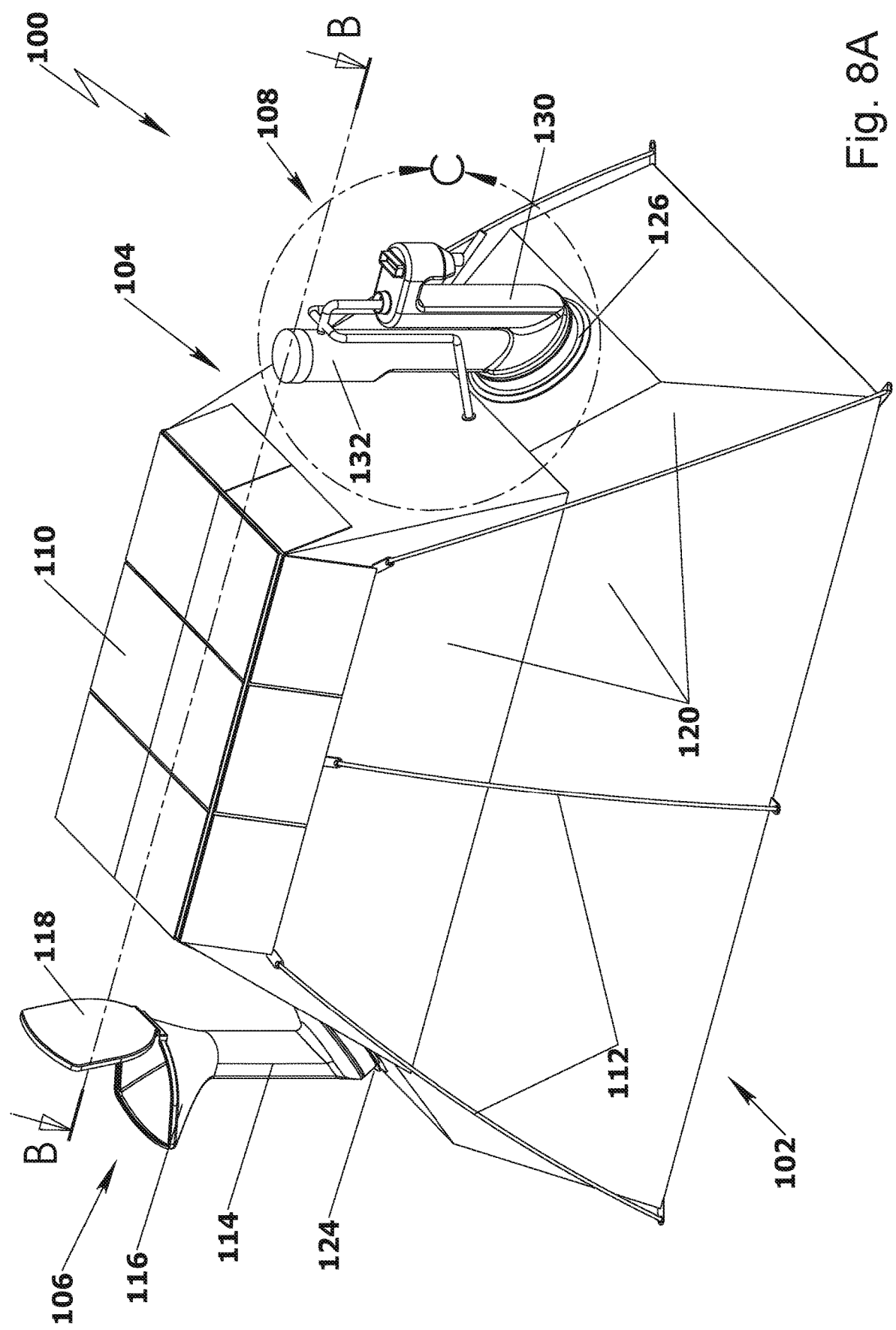
FIG. 8A is an isometric view of a preferred embodiment of the lightweight or extremely lightweight assemblable appliance, supported and shaped by a pliant structured exoskeletal envelope.
Figure 8B:
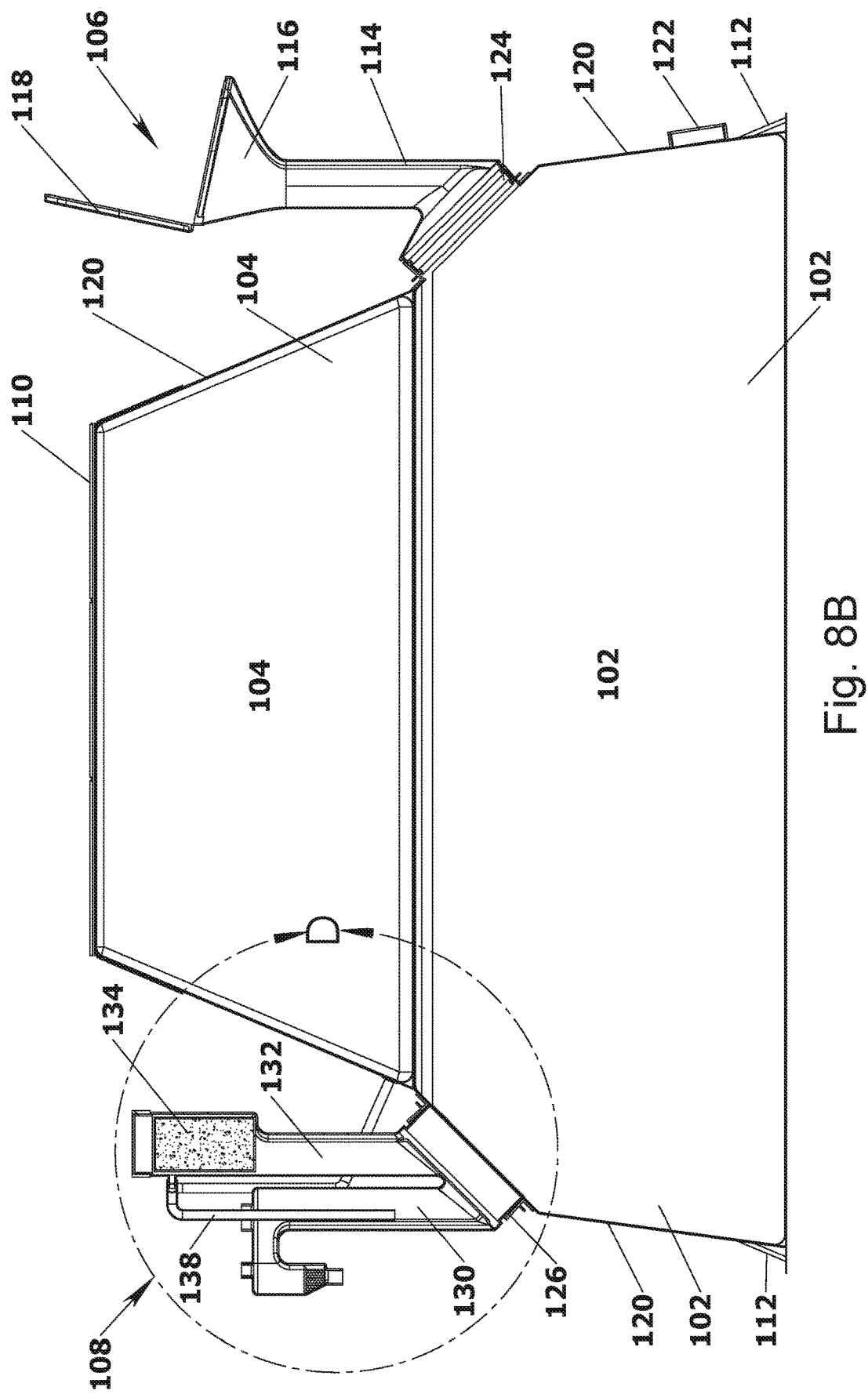
FIG. 8B is a cross-sectional view of a preferred embodiment of the lightweight or extremely lightweight assemblable appliance, supported and shaped by a pliant structured exoskeletal envelope.
Figure 8D:
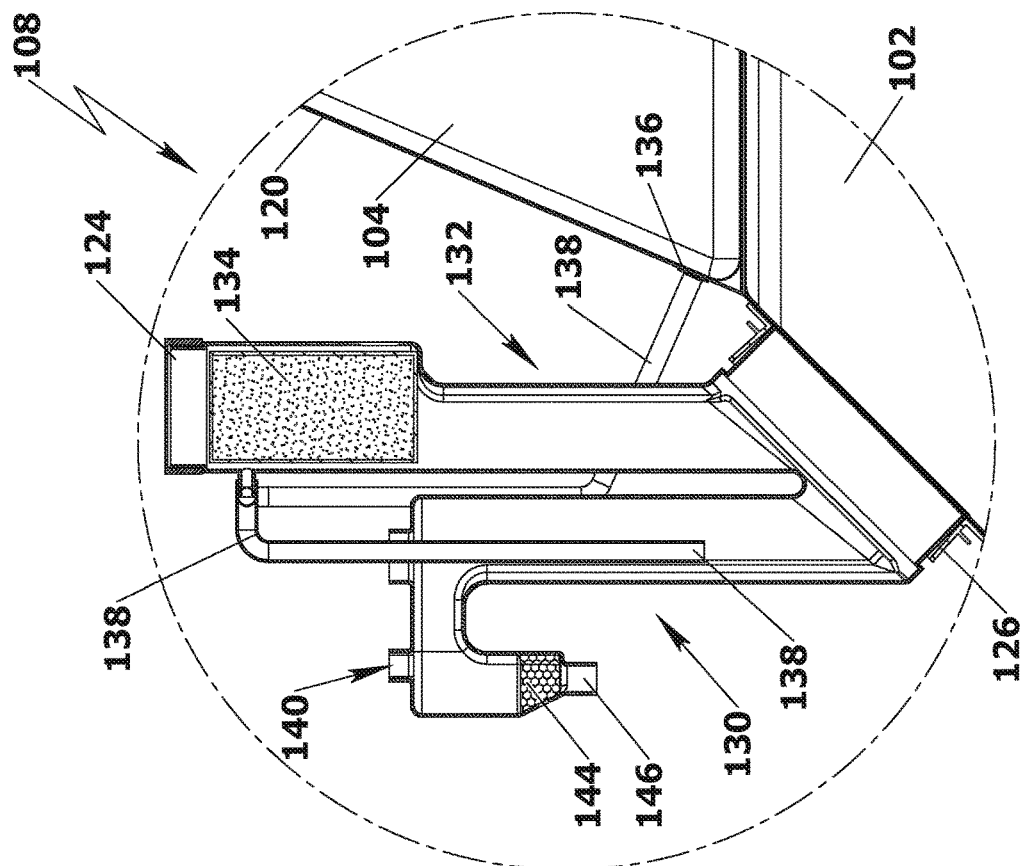
FIG. 8D is an enlarged cross-sectional view showing details of exemplarily outlet assembly of the lightweight or extremely lightweight assemblable appliance, supported and shaped by a pliant structured exoskeletal envelope.
Figure 8C:
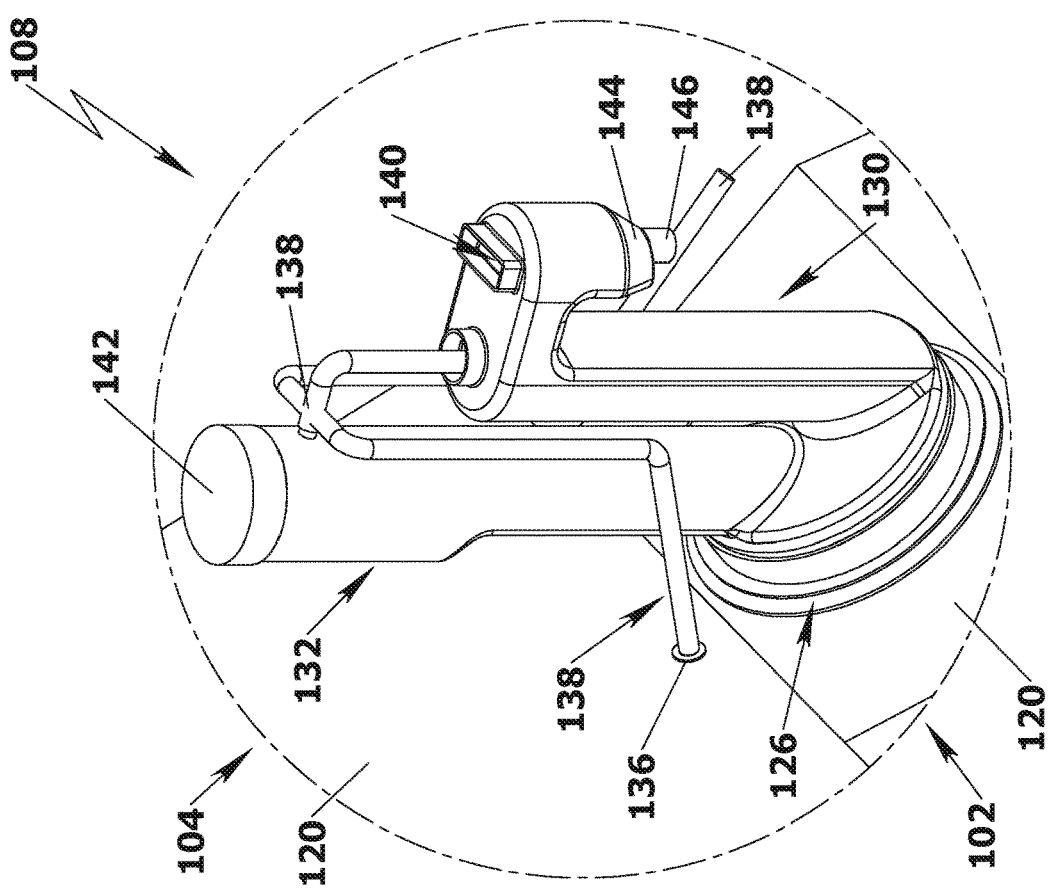
FIG. 8C is an enlarged view showing details of exemplarily outlet assembly of the lightweight or extremely lightweight assemblable appliance, supported and shaped by a pliant structured exoskeletal envelope.

In accordance with some preferred embodiments of the present invention, reference is now made to FIGS. 8A and 8B, showing isometric cross-sectional, views of lightweight or preferably extremely lightweight assemblable appliance 100 as well as to FIG. 8C to 8C, showing enlarged and cross-sectional enlarged views of outlet assembly 108. Appliance 100 comprises anaerobic digester 102 and gas tank 104. Digester 102 and tank 104 are made of elastic, resilient or pliable material.

Referring particularly to FIG. 8A to 8B, appliance 100 further comprises pliant structured exoskeletal envelope 120. Pliant structured exoskeletal envelope 120 defines a frusto-pyramidal shape, where anaerobic digester 102 is accommodated at the bottom portion of the pliant structured exoskeletal envelope 120, whereas gas tank 104 is accommodated at the top portion of the pliant structured exoskeletal envelope 120. Pliant structured exoskeletal envelope 120 confines digester 102 and tank 104 and thereby limits the expansion thereof.

Consequently, upon filling-up anaerobic digester 102 with semiliquid mixture or slurry or ground organic matter or any type of fluid for that matter, in a non-limiting manner including water, grey water and slurry overflow fluid, and/or upon forming positive pressure in gas tank 104, pliant structured exoskeletal envelope 120 is expanded and shaped-up by the pressure exerted from within by digester 102 and tank 104, to assume an erected or deployed confirmation, shown in FIG. 8A to 8B. It is noted that the anaerobic digestion processes, occurring in pliable anaerobic digester 102, resulting a positive pressure in gas tank 104, mainly of methane gas. In some embodiments, organic matter optionally includes for animal droppings, which utilized by lightweight assemblable appliance 100, typically without grinding.

Upon filling-up anaerobic digester 102 with content and forming positive pressure in gas tank 104, pliant structured exoskeletal envelope 120 confers structural firmness to appliance 100, due to a normal counterforce to the force exerted by the faces of digester 102 and tank 104 on exoskeletal envelope 120, somewhat resembling the structural firmness of a wheel tire (not shown) conferred by the expansion of the inner tube (not shown). Pliant exoskeletal envelope 120 embodies a structured shape, configured to accommodate anaerobic digester 102 and gas tank 104, so as to limit their expansion to a maximal predetermined size.

Pliant exoskeletal envelope 120 is preferably made of woven or fibrous fabric, having high tensile strength and capable of being efficiently flexed or bent but incapable of being efficiently stretched or expanded. In some embodiments, pliant structured exoskeletal envelope 120 co-molded or welded with anaerobic digester 102 and/or gas tank 104, to form a monolithic constituent, in which anaerobic digester 102 and/or gas tank 104 are non-detachable pliant structured exoskeletal envelope 120. In other embodiments, pliant structured exoskeletal envelope 120 is an individual constituent distinct from anaerobic digester 102 and/or gas tank 104.

Anaerobic digester 102 comprises anterior flange 124, configured for connecting and mounting anterior inlet assembly 106, implementable for feeding semiliquid mixture, slurry, ground organic matter or a fluid, into anaerobic digester 102. Anterior flange 124 preferably comprises a feeding mechanism, such as a diaphragm or mitral valve (not shown), configured to sustain advancement of semiliquid mixture, slurry, ground organic matter or a fluid, fed into anaerobic digester 102, from anterior inlet assembly 106 but concurrently configured to prevent backflow of the contents from digester 102 into anterior inlet assembly.

Anaerobic digester 102 comprises posterior flange 126, configured for connecting and mounting posterior outlet assembly 108, implementable for draining grey water or overflow slurry fluid from anaerobic digester 102 as well as preferably for conducting the biogas produced by the anaerobic processes in digester 102 to gas tank 104 via conduit 138. Anaerobic digester 102 comprises anterior opening with removable plug 124, configured for occasionally depleting the sludge that may accumulate in digester 102, as a part of maintenance of lightweight assemblable appliance 100.

In order to yet further facilitate an increased pressure inside gas tank 104, appliance 100 further comprises at least one pressure forming mechanism. Embodiments of pressure forming mechanisms in a non-limiting manner include gravitational and/or bias driven devices. Examples of gravitational devices include array of ballast bags or pockets 110, fillable with ballast substance (not shown), configured to facilitate increased pressure by exerting gravitational force onto inside gas tank 104.

Examples of bias driven devices include elastic tension straps 112, comprising an elastomeric material, connected to respective elements attached to the bottom of appliance 100, configured to facilitate increased pressure by exerting tensile strain force onto inside gas tank 104. Notably a combination of gravitational and/or bias driven devices is equally contemplated by this disclosure.

Referring particularly to FIGS. 8C and 8D, anterior inlet assembly 106 comprises feeding conduit 114, which is optionally made of solid, stiff or firm material, capable of supporting its own weight. Feeding conduit 114 terminates with inlet funnel 116, coverable by pivoting and preferably biased lid 118. In some examples feeding conduit 114 is made of flexible or pliant material, incapable of supporting its own weight, in such cases inlet funnel 116 is supported by a bipod (not shown) structure.

Posterior outlet assembly 108 comprises slurry overflow outlet portion 130 and gas ducting portion 132. Slurry overflow outlet portion 130 comprises chlorinator 144, chlorinator filling port 140 and slurry overflow nozzle 146. Slurry overflow nozzle 146 is disposed downstream to chlorinator 144, so that any overflow of slurry from digester 102 to outlet portion 130 passes through chlorinator 144, thereby rendering the fluids outflowing from slurry nozzle 146 non-virulent and biologically safe for the environment or use for irrigation in agriculture.

Gas ducting portion 132 of posterior outlet assembly 108 further comprises biogas filter 134, configured for absorbing sulfurous compounds from the biogas produced in anaerobic digester 102. The biogas filter 134 optionally comprises activated carbon or activated charcoal, which is replaceable from the top opening covered by plug 142. Gas infiltrating through biogas filter 134 is supplied into gas piping 138. Gas piping 138 extends from gas ducting portion 132 of posterior outlet assembly 108 to gas inlet 136 of gas tank 104. Gas piping 138 further extends to a gas-powered consuming appliance (not shown). Gas piping 138 further optionally extends into slurry overflow outlet portion 130. Gas piping further 138 optionally comprises check valves, configured to conduct the biogas only in one direction, and/or safety valves, configured to conduct the biogas only above a predetermined pressure threshold.

Figure 9:
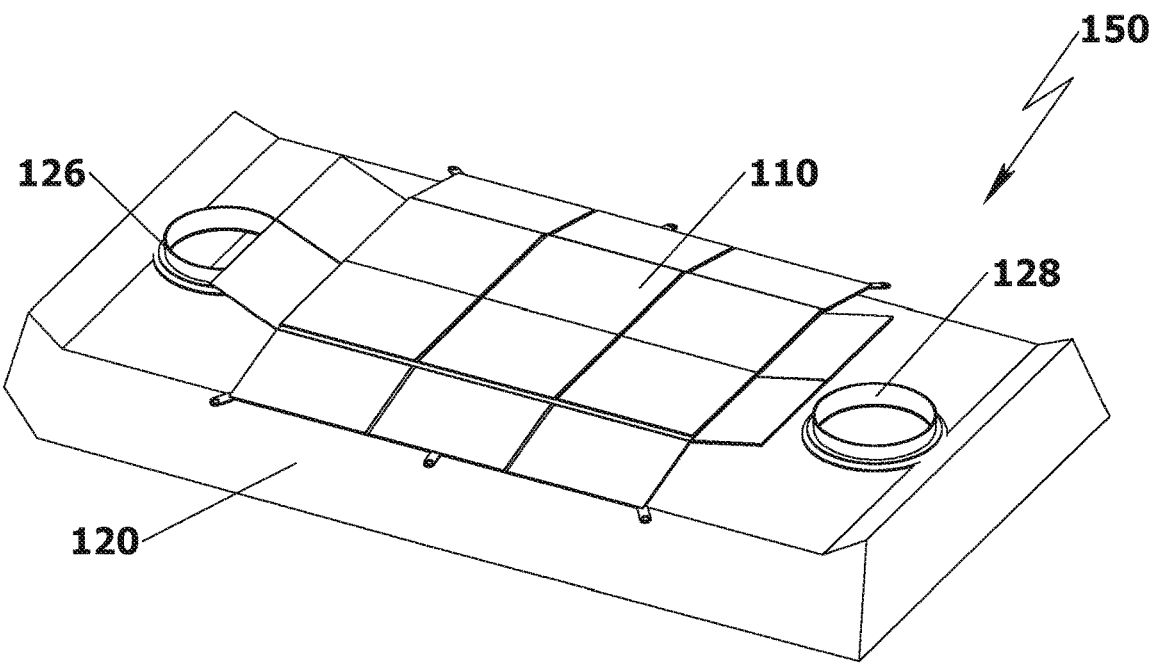
FIG. 9 is an isometric view of a preferred embodiment of the lightweight or extremely lightweight assemblable appliance, in a depleted or collapsed configuration.

Reference is now made to FIG. 9, showing the lightweight or preferably extremely lightweight assemblable appliance in folded or collapsed conformation 150. Lightweight assemblable appliance in folded conformation 150 is configured for assuming a compact size. Lightweight assemblable appliance in folded conformation 150 is typically folded yet further laterally or rolled up to assume a compact size (not shown), configured for shipment and transportation at the back seat of an economy car and/or by air cargo.

Figure 10:
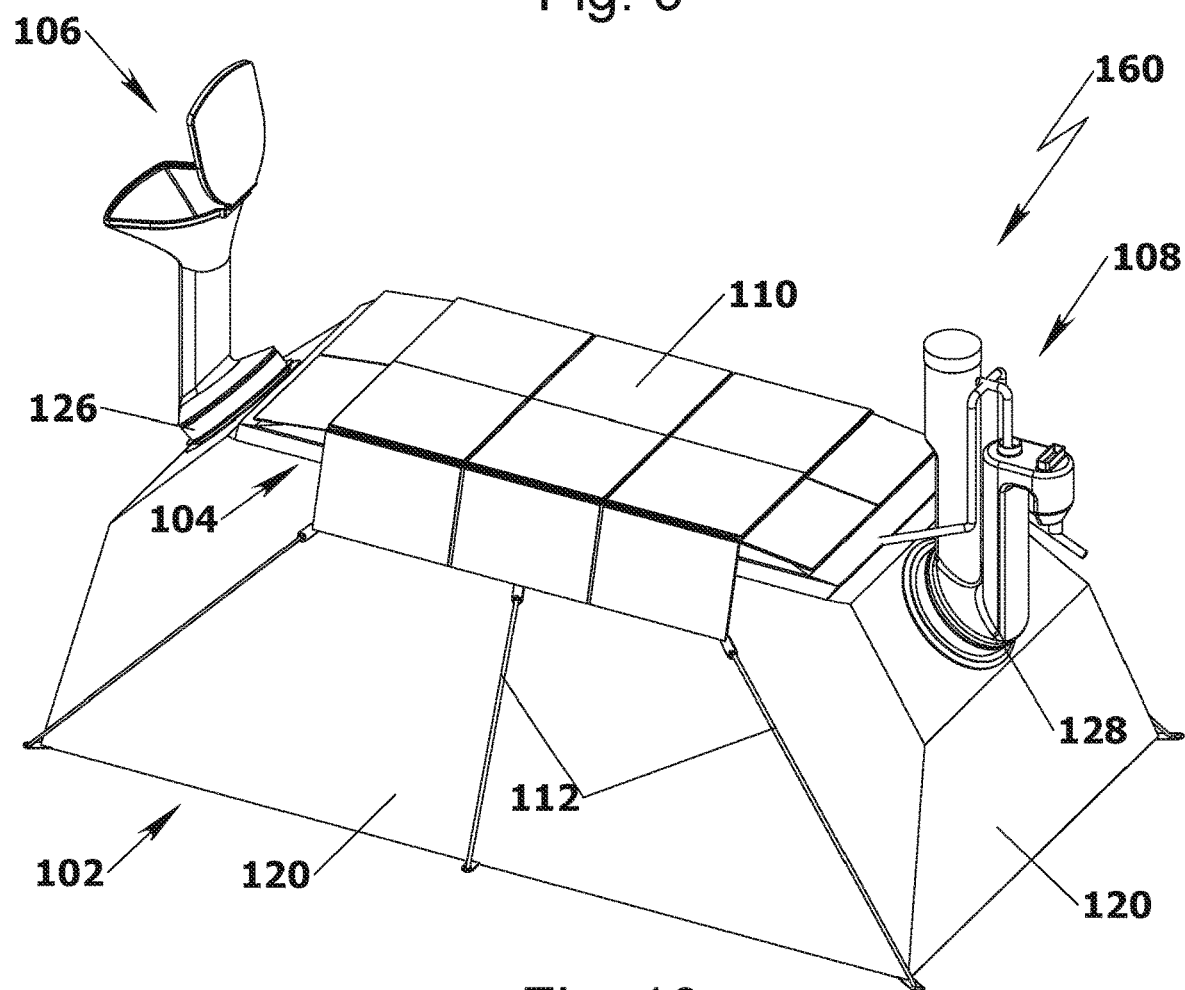
FIG. 10 is an isometric view of a preferred embodiment of the lightweight or extremely lightweight assemblable appliance, wherein the anaerobic digester is in a deployed or erected configuration, whereas the gas tank in a depleted or collapsed configuration.

Reference is now made to FIG. 10, showing the lightweight or preferably extremely lightweight assemblable appliance in a partially erected or deployed conformation 160. Lightweight assemblable appliance assumes a partially erected or deployed conformation 160 upon filling-up anaerobic digester 102 with liquid. Gas tank 104 of lightweight assemblable appliance in a partially erected or deployed conformation 160 is empty of biogas. With the progression of anaerobic processes in anaerobic digester 102, biogas filling-up gas tank 104 and lightweight assemblable appliance assumes completely erected or deployed conformation 100, shown in FIGS. 8A and 8B.

BEST MODE FOR PRACTICING AND CARRYING OUT THE INVENTION

Figure 11:
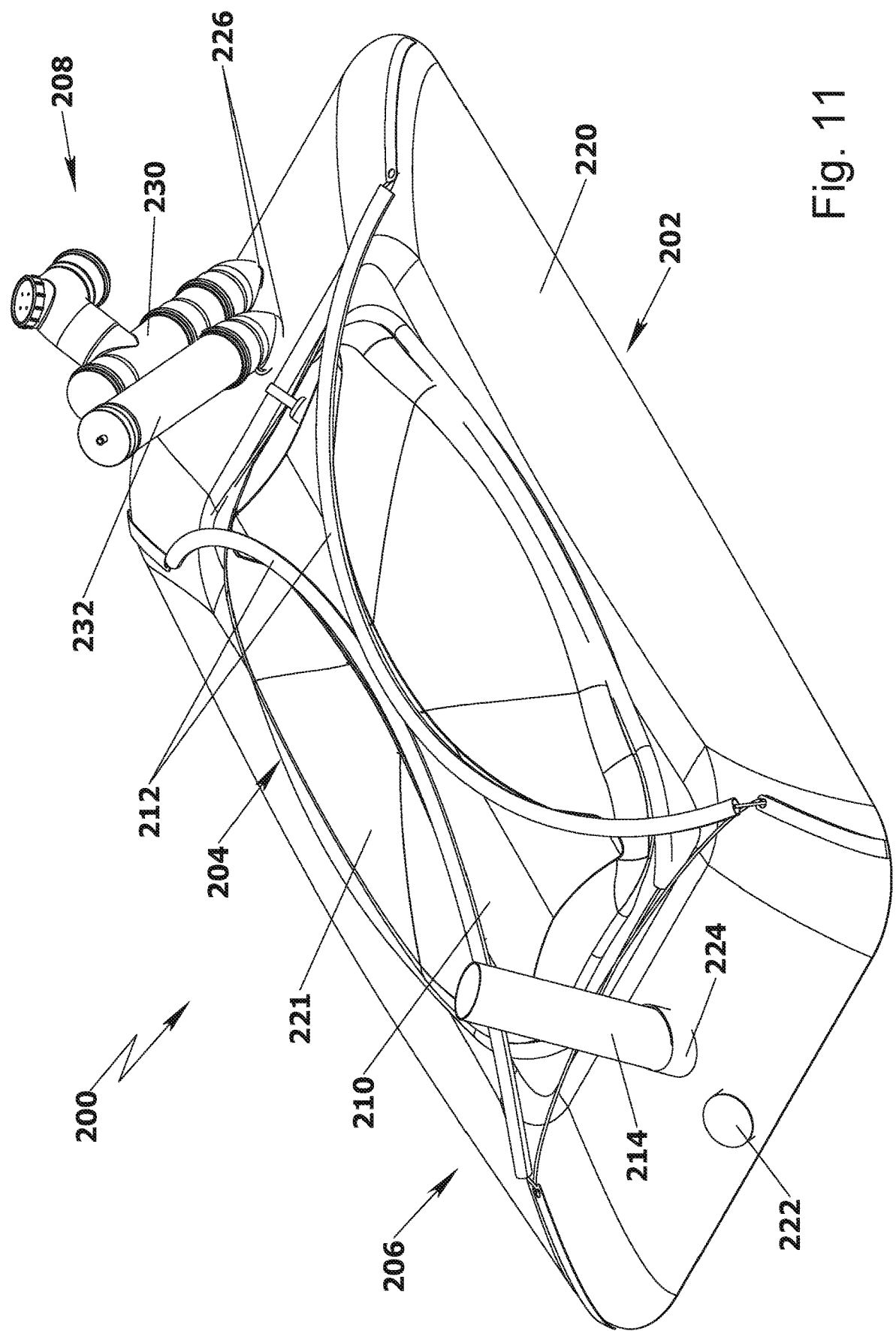
FIG. 11 is an isometric view of a preferred embodiment of the lightweight or extremely lightweight assemblable appliance, in a depleted or collapsed configuration.
Figure 12:
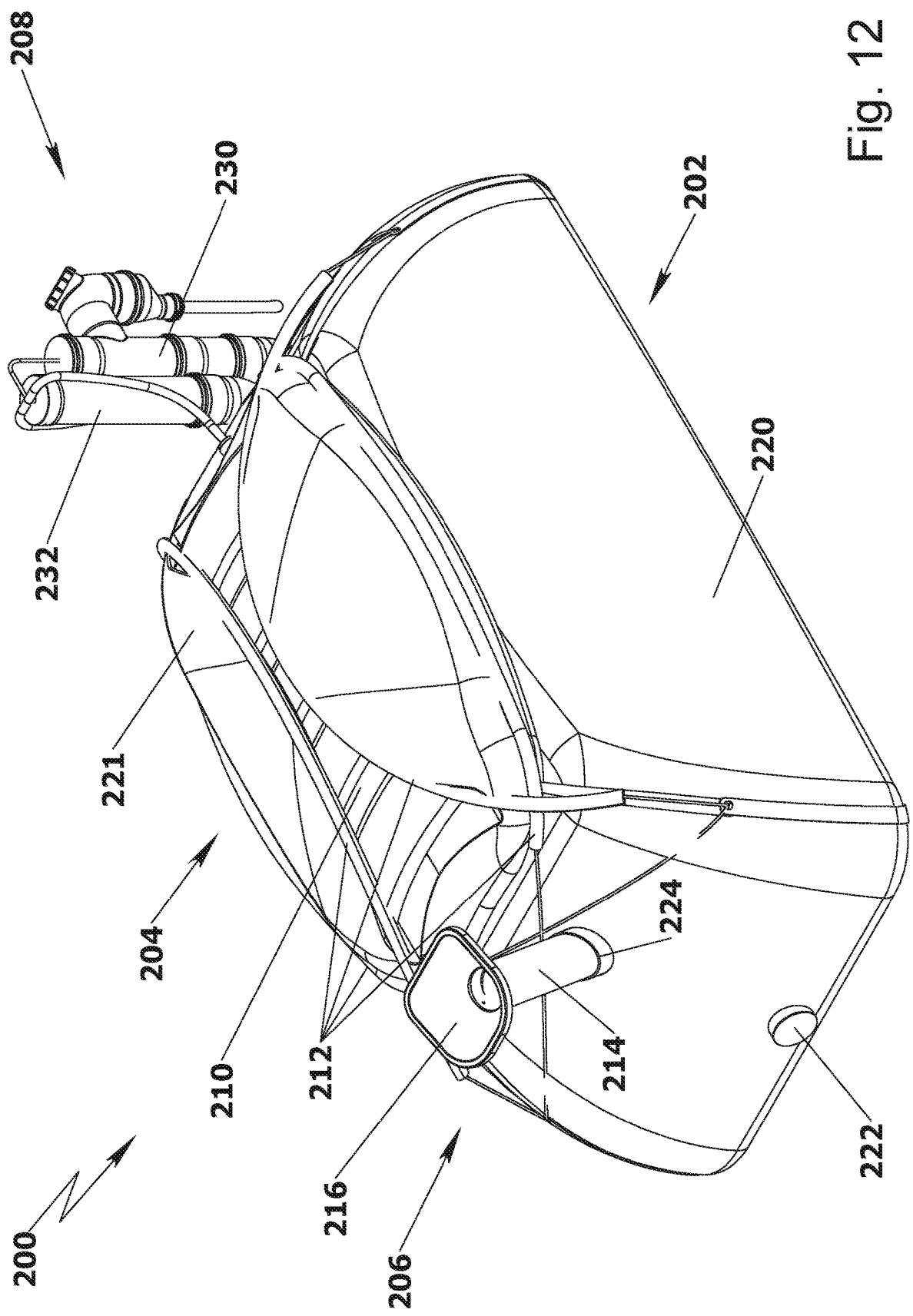
FIG. 12 is an isometric view of a preferred embodiment of the lightweight or extremely lightweight assemblable appliance, wherein the anaerobic digester is in a deployed or erected configuration, whereas the gas tank in a depleted or collapsed configuration.
Figure 13:
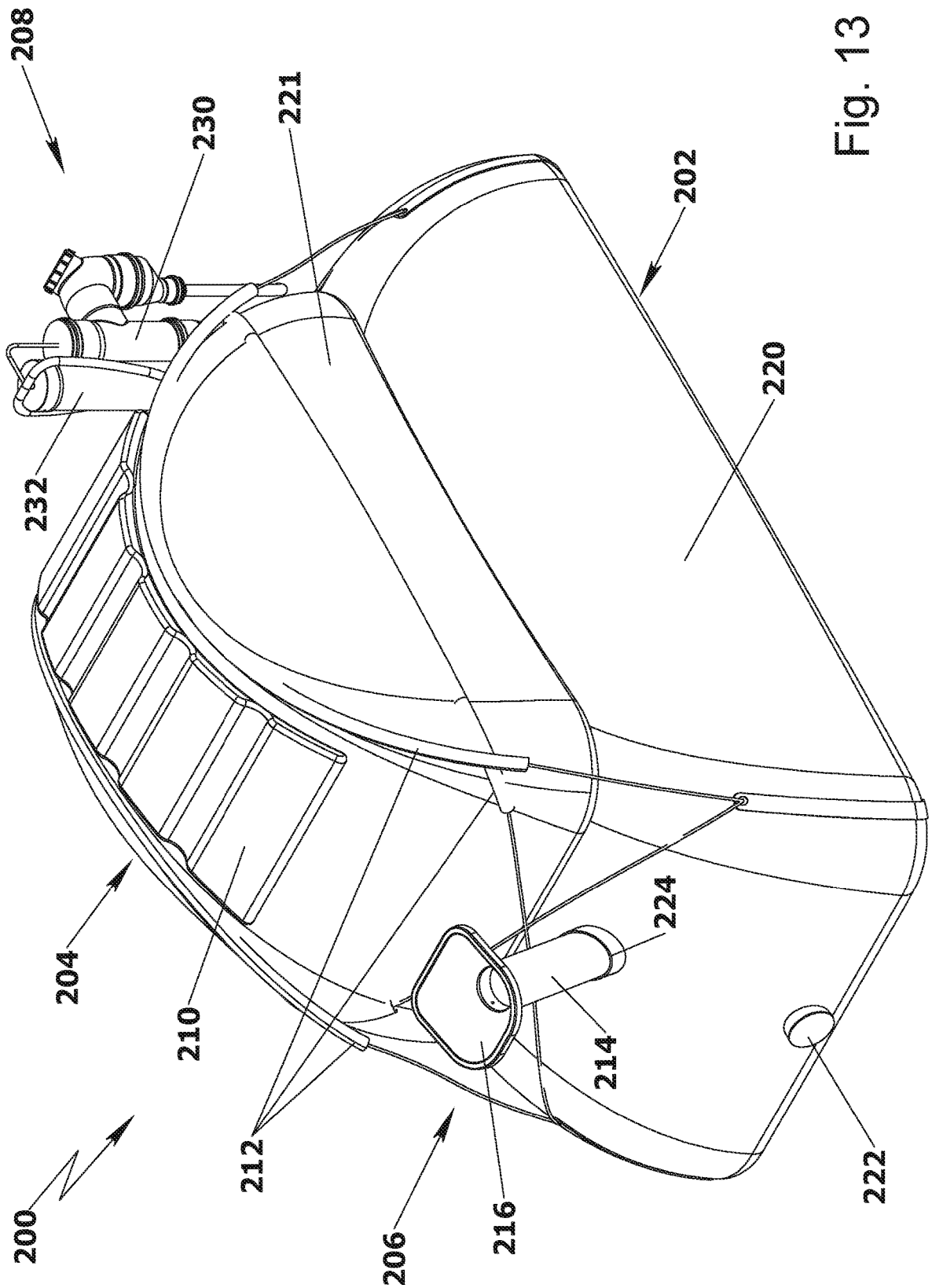
FIG. 13 is an isometric view of a preferred embodiment of the lightweight or extremely lightweight assemblable appliance, supported and shaped by a pliant structured exoskeletal envelope.

In accordance with some preferred embodiments of the present invention, reference is now made to FIGS. 11 to 13, showing isometric views of lightweight or preferably extremely lightweight assemblable appliance 200. Appliance 200 comprises anaerobic digester 202 and gas tank 204. Digester 202 and tank 204 are made of elastic, resilient or pliable material.

Appliance 200 further comprises pliant structured exoskeletal envelope 220 for anaerobic digester 202 and pliant structured exoskeletal envelope 221 for gas tank 204. Pliant structured exoskeletal envelops 220 defines a frusto-pyramidal shape, where anaerobic digester 202 is accommodated, whereas pliant structured exoskeletal envelope 221 defines a frusto-pyramidal shape, where gas tank 104 is accommodated. Pliant structured exoskeletal envelopes 220 and 221 respectively confine digester 202 and tank 204, thereby limiting the expansion thereof.

Consequently, upon filling-up anaerobic digester 202 with semiliquid mixture or slurry or ground organic matter or any type of fluid for that matter, in a non-limiting manner including water, grey water and slurry overflow fluid, and/or upon forming positive pressure in gas tank 204, pliant structured exoskeletal envelopes 220 and 221 are expanded and shaped-up by the pressure exerted from within by digester 202 and tank 204, to assume an erected or deployed confirmation, shown in FIG. 13. It is noted that the anaerobic digestion processes, occurring in pliable anaerobic digester 202, resulting a positive pressure in gas tank 204, mainly of methane gas. In some embodiments, organic matter optionally includes for animal droppings, which utilized by lightweight assemblable appliance 200, typically without grinding.

Upon filling-up anaerobic digester 202 with content and forming positive pressure in gas tank 204, pliant structured exoskeletal envelope 220 and 221 confer structural firmness to appliance 200, due to a normal counterforce to the force exerted by the faces of digester 202 and tank 204 on exoskeletal envelopes 220 and 221, somewhat resembling the structural firmness of a wheel tire (not shown) conferred by the expansion of the inner tube (not shown). Pliant exoskeletal envelopes 220 and 221 embody structured shapes, configured to accommodate anaerobic digester 202 and gas tank 204, so as to limit their expansion to a maximal predetermined size.

Pliant exoskeletal envelopes 220 and 221 are preferably made of woven or fibrous fabric, having high tensile strength and capable of being efficiently flexed or bent but incapable of being efficiently stretched or expanded. In some embodiments, pliant structured exoskeletal envelopes 220 and 221 are co-molded or welded with anaerobic digester 202 and/or gas tank 204, to form a monolithic constituent, in which anaerobic digester 202 and/or gas tank 204 are non-detachable pliant structured exoskeletal envelopes 220 and 221.

In some preferred embodiments, pliant structured exoskeletal envelopes 220 and 221 are co-molded or welded with anaerobic digester 202 and/or gas tank 204, so that envelopes 220 and 221 as well as digester 202 and/or gas tank 204 comprise composite materials. A preferred instance of composite material used for manufacture the complex of exoskeletal envelope 220 and anaerobic digester 202 is a multilayered PVC sheet with embedded nylon or other polymeric pliable fibers.

In some embodiments, pliant structured exoskeletal envelopes 220 and 221 are a unified singular pliant structured exoskeletal envelope, such as envelope 120 shown in FIGS. 8 to 10. In other embodiments, pliant structured exoskeletal envelopes 220 and 221 are individual constituents distinct from anaerobic digester 202 and/or gas tank 204.

Anaerobic digester 202 comprises anterior flange 224, configured for connecting and mounting anterior inlet assembly 206, implementable for feeding semiliquid mixture, slurry, ground organic matter or a fluid, into anaerobic digester 202. Anterior flange 224 preferably comprises a feeding mechanism, such as a diaphragm or mitral valve (not shown), configured to sustain advancement of semiliquid mixture, slurry, ground organic matter or a fluid, fed into anaerobic digester 202, from anterior inlet assembly 206 but concurrently configured to prevent backflow of the contents from digester 202 into anterior inlet assembly.

Anaerobic digester 202 comprises posterior flanges 226, configured for connecting and mounting posterior outlet assembly 208, implementable for draining grey water or overflow slurry fluid from anaerobic digester 202 as well as for conducting the biogas produced by the anaerobic processes in digester 202 to gas tank 204. Anaerobic digester 202 comprises anterior opening 222 with removable plug, configured for occasionally depleting the sludge that may accumulate in digester 202, as a part of maintenance of lightweight assemblable appliance 200.

In order to yet further facilitate an increased pressure inside gas tank 204, appliance 200 further comprises at least one pressure forming mechanism. Embodiments of pressure forming mechanisms in a non-limiting manner include gravitational and/or bias driven devices. Examples of gravitational devices include array of ballast bags or pockets 210, fillable with ballast substance (not shown), configured to facilitate increased pressure by exerting a gravitational force onto gas tank 204.

Examples of bias driven devices include elastic tension straps 212, comprising an elastomeric material, connected to respective elements attached to the bottom of appliance 200, configured to facilitate increased pressure by exerting tensile strain force onto inside gas tank 204. Notably a combination of gravitational and/or bias driven devices is equally contemplated by this disclosure.

Anterior inlet assembly 206 comprises feeding conduit 214, which is optionally made of solid, stiff or firm material, capable of supporting its own weight. Feeding conduit 214 terminates with inlet funnel 216, preferably coverable by pivoting and preferably biased lid (not shown). In some examples feeding conduit 214 is made of flexible or pliant material, incapable of supporting its own weight, in such cases inlet funnel 216 is supported by a bipod (not shown) structure.

Posterior outlet assembly 208 comprises slurry overflow outlet portion 230 and gas ducting portion 232. Slurry overflow outlet portion 230 preferably comprises a chlorinator (not shown) with a chlorinator filling port and a slurry overflow nozzle. The slurry overflow nozzle is disposed downstream to the chlorinator (not shown), so that any overflow of slurry from digester 202 to outlet portion 230 passes through the chlorinator (not shown), thereby rendering the fluids outflowing from the slurry nozzle non-virulent and biologically safe for the environment or use for irrigation in agriculture.

Gas ducting portion 232 of posterior outlet assembly 208 further comprises biogas filter (not shown), configured for absorbing sulfurous compounds from the biogas produced in anaerobic digester 202. The biogas filter (not shown) optionally comprises activated carbon or activated charcoal, which is replaceable from the top opening covered by a plug (not shown). Gas infiltrating through a biogas filter (not shown) is supplied into gas piping (not shown). The gas piping (not shown) extends from gas ducting portion 232 of posterior outlet assembly 208 to the gas inlet (not shown) of gas tank 204. The gas piping (not shown) further extends to a gas-powered consuming appliance (not shown). The gas piping (not shown) further optionally extends into slurry overflow outlet portion 230. The gas piping further (not shown) optionally comprises check valves, configured to conduct the biogas only in one direction, and/or safety valves, configured to conduct the biogas only above a predetermined pressure threshold.

Reference is now made to FIG. 11, showing the lightweight or preferably extremely lightweight assemblable appliance 200 in folded or collapsed conformation. Lightweight assemblable appliance 200 in folded conformation, shown in FIG. 11, is configured for assuming a compact size. Lightweight assemblable appliance 200, shown in FIG. 11, in folded conformation is typically folded yet further laterally or rolled up to assume a compact size (not shown), configured for shipment and transportation at the back seat of an economy car and/or by air cargo.

Reference is now made to FIG. 12, showing the lightweight or preferably extremely lightweight assemblable appliance 200 in a partially erected or deployed conformation. Lightweight assemblable appliance assumes a partially erected or deployed conformation, shown in FIG. 12, upon filling-up anaerobic digester 202 with liquid. Gas tank 204 of lightweight assemblable appliance 200 in a partially erected or deployed conformation, shown in FIG. 12, is empty of biogas. With the progression of anaerobic processes in anaerobic digester 202, biogas filling-up gas tank 204 and lightweight assemblable appliance 200 assumes completely erected or deployed conformation, shown in FIG. 13.

Wherever in the specification hereinabove and in claims hereunder it is noted that the pliable collapsible anaerobic digester, such as digesters 50, 102 or 202, including or comprising an inlet pipe, gas outlet pipe, slurry overflow outlet pipe or sludge outlet draining pipe—it should be construed that the pliable collapsible anaerobic digester includes or comprises merely a preparation on the surface thereof and/or inside the wall thereof as well as an additional element for relatively easily mounting and/or attaching an inlet pipe, gas outlet pipe, slurry overflow outlet pipe or sludge outlet draining pipe thereto, whereas the inlet pipe, gas outlet pipe, slurry overflow outlet pipe or sludge outlet draining pipe are not provided or attached to the digester.

It will be appreciated by persons skilled in the art that the present invention is not limited by what has been particularly shown and described herein above. Rather the scope of the invention is defined by the claims which follow:

What is claimed is:

1. An assemblable appliance for recycling organic waste into biogas and liquid fertilizer, implementing essentially anaerobic digestion processes, said assemblable appliance is operable as an autonomic standalone unit, said assemblable appliance comprises:
   (a) at least one pliant structured exoskeletal envelope, comprising a pliable collapsible anaerobic digester configured for transportation in a compact form, comprising:
      (I) a structured shape;
      (II) at least one tensile element characterized by a relatively high tensile strength;
      III a sheet of pliable material, forming an essentially closed structure characterized by a relatively low tensile strength wherein said relatively low tensile strength of said sheet of said pliable material is lower than said relatively high tensile strength of said at least one tensile element;
      (IV) a plurality of apertures for connectors of said device;
      V an inlet configured for feeding a semiliquid mixture of organic matter and water into said anaerobic digester;
      VI a gas outlet, hermetically attached to an upper portion of said anaerobic digester;
      VII a slurry overflow outlet, extending from a sidewall of said anaerobic digester;
   (b) a collapsible gas tank comprising:
      (I) a sheet of pliable material, forming an essentially closed was tank structure, characterized by a relatively low tensile strength, wherein said relatively low tensile strength of said sheet of said pliable material of said gas tank is lower than said relatively high tensile strength of said at least one tensile element;
      (II) at least one element selected from the group consisting of: a gas inlet, and a gas outlet;
      (III) at least one pressure exerting mechanism configured to facilitate increased pressure in said collapsible gas tank, said at least one pressure exerting mechanism is selected from the group consisting of: elastic tension straps, comprising an elastomeric material, connectable to connectors elements attached to said appliance, and a flexible elongated and foldable ballast bag, fillable with ballast substance, said flexible elongated ballast bag is configured for assuming a conformation, respectively matching the shape of said collapsible gas tank; wherein said assemblable appliance is characterized by lacking any rigid structural support scaffolding.

2. The assemblable appliance, as set forth in claim 1, further comprises at least one component; of a feeding sub-assembly, selected from the group consisting of:
   (a) a feeding conduit comprising a solid, stiff or firm material, capable of supporting its own weight, connected to inlet of said pliable collapsible anaerobic digester;
   (b) a feeding conduit comprising a flexible or pliant material, incapable of supporting its own weight, in combination with a support structure;
   (c) a feeding funnel configured for feeding said organic waste into said feeding conduit;
   (d) a grinder, configured to grind said organic waste into said semiliquid mixture;
   (e) a sink cover characterized by a sloped or slated shape, thereby facilitating feeding said organic waste into said anaerobic digester;
   (f) a water canister, for supplying a water fraction for said semiliquid mixture;
   (g) a water tap for controlling the amount of said water fraction in said semiliquid mixture.

3. The assemblable appliance, as set forth in claim 1, further comprises a means of feeding said semiliquid mixture under pressure into said inlet of said pliable collapsible anaerobic digester.

4. The assemblable appliance, as set forth in claim 1, wherein said structured shape is a frusto-pyramidal or frusto-conical structured shape.

5. The assemblable appliance, as set forth in claim 1, wherein said a gas outlet of said anaerobic digester and said slurry overflow outlet of said anaerobic digester are essentially a unified singular opening in said anaerobic digester.

6. The assemblable appliance, as set forth in claim 1, wherein said at least one tensile element is co-molded with or welded to or fused with or reinforcing said sheet of pliable material; thereby forming an essentially unified or monolithic structure.

7. The assemblable appliance, as set forth in claim 1, wherein said at least one pliant structured exoskeletal envelope comprises:
   (a) a first dedicated pliant structured exoskeletal envelope configured for enclosing said pliable collapsible anaerobic digester;
   (b) a second dedicated pliant structured exoskeletal envelope configured for enclosing said collapsible gas tank.

8. A method of recycling organic waste into biogas and liquid fertilizer, implementing essentially anaerobic digestion processes; by a means of assemblable appliance, said method comprises:
   (a) providing a compact kit-of-parts, configured for transportation in a folded form, said kit-of-parts comprising:
      (I) least one pliant structured exoskeletal envelope, comprising a pliable collapsible anaerobic digester configured for transportation in a compact form, said pliant structured exoskeletal envelope comprising:
         (i) a structured shape;
         (ii) at least one tensile element characterized by a relatively high tensile strength;
         (iii) a plurality of apertures for connectors of said appliance;
         (iv) a sheet of pliable material, forming an essentially, closed structure, characterized by a relatively low tensile strength wherein said relatively low tensile strength of said sheet of said pliable material of said gas tank is lower than said relatively high tensile strength of said at least one tensile element;
         (v) a plurality of apertures for connectors of said device;
         (vi) an inlet configured for feeding a semiliquid mixture of organic matter and water into said anaerobic digester;
         (vii) a gas outlet, hermetically attached to an upper portion of said anaerobic digester;
         (viii) a slurry overflow outlet, extending from a sidewall of said anaerobic digester;

(ix) a sludge draining outlet, extending from a bottom portion of a sidewall of said anaerobic digester;
(II) a collapsible gas tank comprising:
(i) a sheet of pliable material, forming an essentially closed gas tank structure, characterized by a relatively low tensile strength wherein said relatively low tensile strength of said sheet of said pliable material is lower than said relatively high tensile strength of said at least one tensile element;
(ii) at least one element selected from the group consisting of: a gas inlet, and a gas outlet;
(iii) at least one pressure exerting mechanism configured to facilitate increased pressure in said collapsible gas tank said at least one pressure exerting mechanism is selected from the group consisting of: elastic tension straps, comprising an elastomeric material, connectable to connectors elements attached to said appliance, and a flexible elongated and foldable ballast bag, fellable with a ballast substance, said flexible elongated ballast bag is configured assuming a conformation, respectively matching the shape of said collapsible gas tank;
wherein said assemblable appliance is characterized by lacking any rigid structural support scaffolding;
(b) assembling said lightweight structural appliance from said kit-of-parts;
(c) feeding a semiliquid mixture or slurry of ground organic matter and water into said pliable collapsible anaerobic digester;
(d) sustaining essentially anaerobic digestion processes in said pliable collapsible anaerobic digester.

9. The method of recycling organic waste, as set forth in claim 8, wherein said assemblable appliance further comprises at least one component, of a feeding sub-assembly, selected from the group consisting of:
(a) a feeding conduit comprising a solid, stiff or firm material, capable of supporting its own weight, connected to inlet of said pliable collapsible anaerobic digester;
(b) a feeding conduit comprising a flexible or pliant material, incapable of supporting its own weight, in combination with a support structure;
(c) a feeding funnel configured for feeding said organic waste into said feeding conduit;
(d) a grinder, configured to grind said organic waste into said semiliquid mixture;
(e) a sink cover characterized by a sloped or slated shape, thereby facilitating feeding said organic waste into said anaerobic digester;
(f) a water canister, for supplying a water fraction for said semiliquid mixture;
(g) a water tap for controlling the amount of said water fraction in said semiliquid mixture.

10. The method of recycling organic waste, as set forth in claim 8, further comprises a means of feeding said semiliquid mixture under pressure into said inlet of said pliable collapsible anaerobic digester.

11. The method of recycling organic waste, as set forth in claim 8, wherein said structured shape is a frusta-pyramidal or frusto-conical structured shape.

12. The method of recycling organic waste, as set forth in claim 8, wherein said gas outlet of said anaerobic digester and said slurry overflow outlet of said anaerobic digester are essentially a unified singular opening in said anaerobic digester.

13. The method of recycling organic waste, as set forth in claim 8, wherein said pliant structured exoskeletal envelope is co-molded with or welded to at least one member selected from the group consisting of: said anaerobic digester and said gas tank; thereby forming an essentially unified or monolithic structure with said at least one member.

14. The method of recycling organic waste, as set forth in claim 13, wherein said at least one pliant structured exoskeletal envelope comprises:
(a) a first dedicated pliant structured exoskeletal envelope configured for enclosing said pliable collapsible anaerobic digester;
(b) a second dedicated pliant structured exoskeletal envelope configured for enclosing said collapsible gas tank.

15. A compact kit-of-parts of an assemblable appliance for recycling organic waste into biogas and liquid fertilizer, implementing essentially anaerobic digestion processes, configured for transportation in a compact form, said kit-of-parts comprises:
(a) at least one pliant structured exoskeletal envelope, comprising a pliable collapsible anaerobic digester configured for transportation in a compact form, comprising:
(I) a structured shape;
(II) at least one tensile element characterized by a relatively high tensile strength;
(III) a plurality of apertures for connectors of said appliance;
(IV) a sheet of pliable material, characterized by a relatively low tensile strength, wherein said relatively low tensile strength of said sheet of said pliable material is lower than said relatively high tensile strength of said at least one tensile element;
(V) an inlet configured for feeding a semiliquid mixture of organic matter and water into said anaerobic digester;
(VI) a gas outlet, hermetically attached to an upper portion of said anaerobic digester;
(VII) a slurry overflow outlet, extending from a sidewall of said anaerobic digester;
(VIII) a sludge draining outlet, extending from a bottom portion of a sidewall of said anaerobic digester;
(b) a collapsible gas tank comprising:
(I) a sheet of pliable material, forming an essentially closed gas tank structure, characterized by a relatively low tensile strength wherein said relatively low tensile strength of said sheet of said pliable material of said gas tank is lower than said relatively high tensile strength of said at least one tensile element;
(II) at least one element selected from the group consisting of: a gas inlet, and a gas outlet;
(c) at least one pressure exerting mechanism configured to facilitate increased pressure in said collapsible gas tank, said at least one pressure exerting mechanism is selected from the group consisting of: elastic tension straps, comprising an elastomeric material, connectable to connectors elements attached to said appliance, and a flexible elongated and foldable ballast bag, finable with ballast substance, said flexible elongated ballast bag is configured assuming a conformation, respectively matching the shape of said collapsible gas tank;
said kit-of-parts is characterized by lacking any rigid structural support members.

16. The kit-of-parts, as set forth in claim 15, further comprises at least one component, of a feeding sub-assembly, selected from the group consisting of:

(a) a feeding conduit comprising a solid, stiff or firm material, capable of supporting its own weight, connected to inlet of said pliable collapsible anaerobic digester;
(b) a feeding conduit comprising a flexible or pliant material, incapable of supporting its own weight, in combination with a support structure;
(c) a feeding funnel configured for feeding said organic waste into said feeding conduit;
(d) a grinder, configured to grind said organic waste into said semiliquid mixture;
(e) a sink cover characterized by a sloped or slated shape; thereby facilitating feeding said organic waste into said anaerobic digester;
(f) a water canister, for supplying a water fraction for said semiliquid mixture;
(g) a water tap for controlling the amount of said water fraction in said semiliquid mixture.

17. The kit-of-parts, as set forth in claim 15, further comprises a means of feeding said semiliquid mixture into said inlet of said pliable collapsible anaerobic digester.

18. The kit-of-parts, as set forth in claim 15, wherein said structured shape is a frusto-pyramidal or frusto-conical structured shape.

19. The kit-of-parts, as set forth in claim 15, wherein said pliant structured exoskeletal envelope is co-molded with or welded to at least one member selected from the group consisting of: said anaerobic digester and said gas tank; thereby forming an essentially unified or monolithic structure with said at least one member.

20. The kit-of-parts, as set forth in claim 19, wherein said at least one pliant structured exoskeletal envelope comprises:

(a) a first dedicated pliant structured exoskeletal envelope configured for enclosing said pliable collapsible anaerobic digester;
(b) a second dedicated pliant structured exoskeletal envelope configured for enclosing said collapsible gas tank.

* * * * *